(12) United States Patent
Anvari

(10) Patent No.: US 11,031,106 B2
(45) Date of Patent: Jun. 8, 2021

(54) USE OF 5G IOT NETWORK FOR A VIRTUAL MEDICAL SYSTEM

(71) Applicant: Kiomars Anvari, Walnut Creek, CA (US)

(72) Inventor: Kiomars Anvari, Walnut Creek, CA (US)

(73) Assignee: Kiomars Anvari, Walnut Creek, CA (US)

( * ) Notice: Subject to any disclaimer, the term of this patent is extended or adjusted under 35 U.S.C. 154(b) by 0 days.

(21) Appl. No.: 16/828,013

(22) Filed: Mar. 24, 2020

(65) Prior Publication Data

US 2020/0286598 A1 Sep. 10, 2020

Related U.S. Application Data

(63) Continuation-in-part of application No. 16/743,354, filed on Jan. 15, 2020, and a continuation-in-part of application No. 16/101,500, filed on Aug. 12, 2018, now abandoned.

(51) Int. Cl.
| | |
|---|---|
| *G16H 10/40* | (2018.01) |
| *H04W 4/80* | (2018.01) |
| *G16H 20/60* | (2018.01) |
| *G16H 10/60* | (2018.01) |

(52) U.S. Cl.
CPC .......... *G16H 10/40* (2018.01); *G16H 10/60* (2018.01); *G16H 20/60* (2018.01); *H04W 4/80* (2018.02)

(58) Field of Classification Search
CPC ........... G16H 1/40; G16H 1/60; G16H 20/60; H04W 4/80

USPC .......................................................... 705/2–3
See application file for complete search history.

(56) References Cited

U.S. PATENT DOCUMENTS

| | | | | |
|---|---|---|---|---|
| 7,062,076 B1* | 6/2006 | Osborne | ............ | G06K 9/00127 382/128 |
| 8,712,790 B1* | 4/2014 | Brown | .................... | G06Q 10/10 705/2 |
| 2004/0059603 A1* | 3/2004 | Brown, Jr. | ............. | G16H 10/60 705/2 |
| 2007/0293733 A1* | 12/2007 | Quy | ......................... | G16H 20/30 600/300 |
| 2009/0069643 A1* | 3/2009 | Quy | ........................ | G16H 20/30 600/300 |
| 2009/0177495 A1* | 7/2009 | Abousy | ................... | G16H 50/20 705/3 |
| 2011/0301982 A1* | 12/2011 | Green, Jr. | ............... | G06Q 10/06 705/3 |
| 2014/0081662 A1* | 3/2014 | Bradrick | ............ | A61B 5/14503 705/3 |

(Continued)

*Primary Examiner* — Michael Tomaszewski

(57) ABSTRACT

Fifth generation wireless systems (5G) are on the horizon and IoT is taking the center stage as devices are expected to form a major portion of this 5G network paradigm. IoT technologies such as machine to machine communication complemented with intelligent data analytics are expected to drastically change landscape of various industries. This application discloses a novel approach (virtual) to medical system using IoT network and artificial intelligence. It instantly allows patients to obtain information data about their medical status and recommendations for the steps they need to take. This method eliminates a lot of the steps the patient needs to take in present medical systems.

16 Claims, 22 Drawing Sheets

(56) References Cited

U.S. PATENT DOCUMENTS

| | | | |
|---|---|---|---|
| 2015/0238692 A1* | 8/2015 | Peterson ................ | G16H 20/30 |
| | | | 604/503 |
| 2017/0300654 A1* | 10/2017 | Stein .................. | H04B 7/18528 |
| 2018/0055384 A1* | 3/2018 | Ambili ................. | A61B 5/0816 |

* cited by examiner

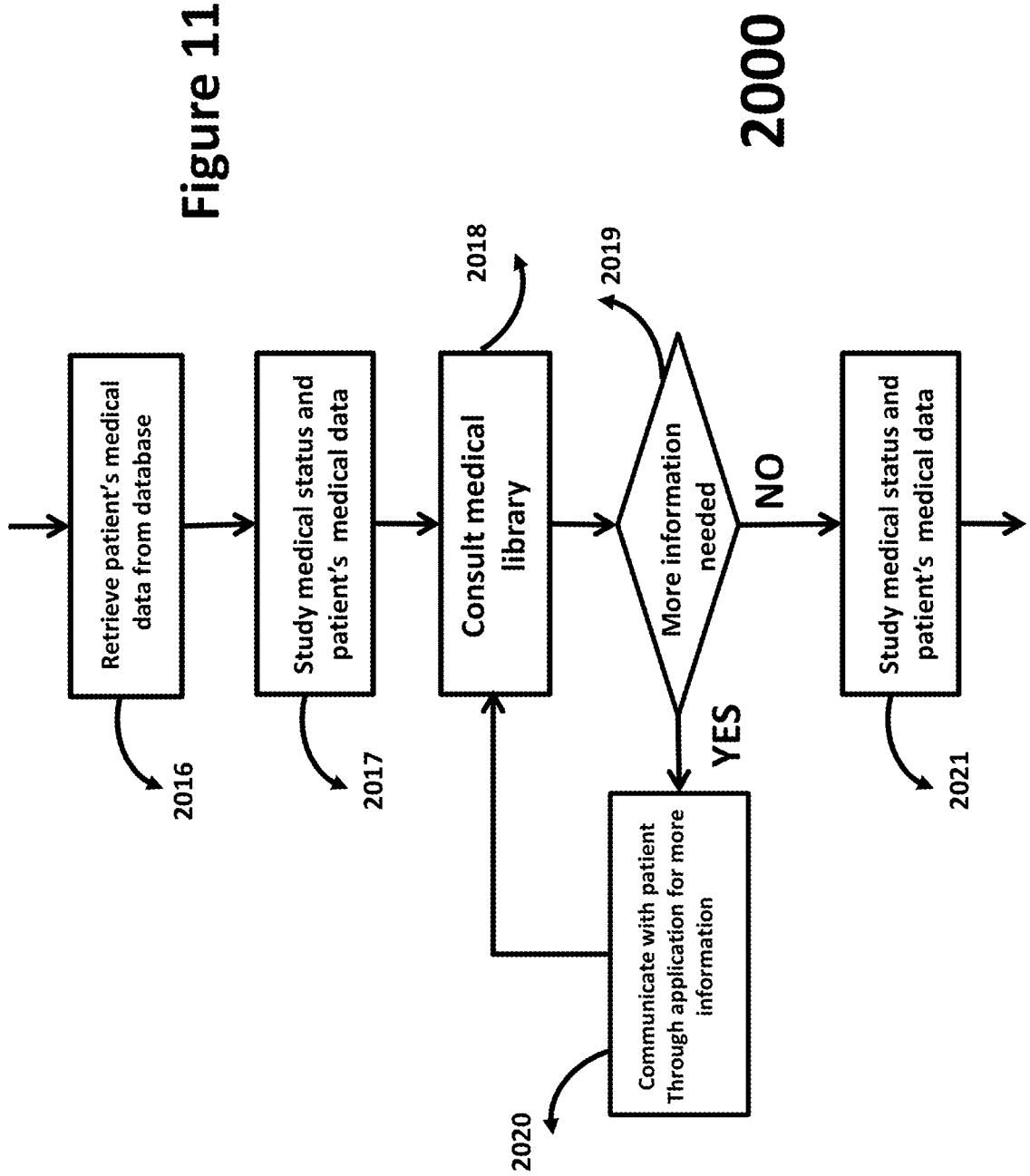

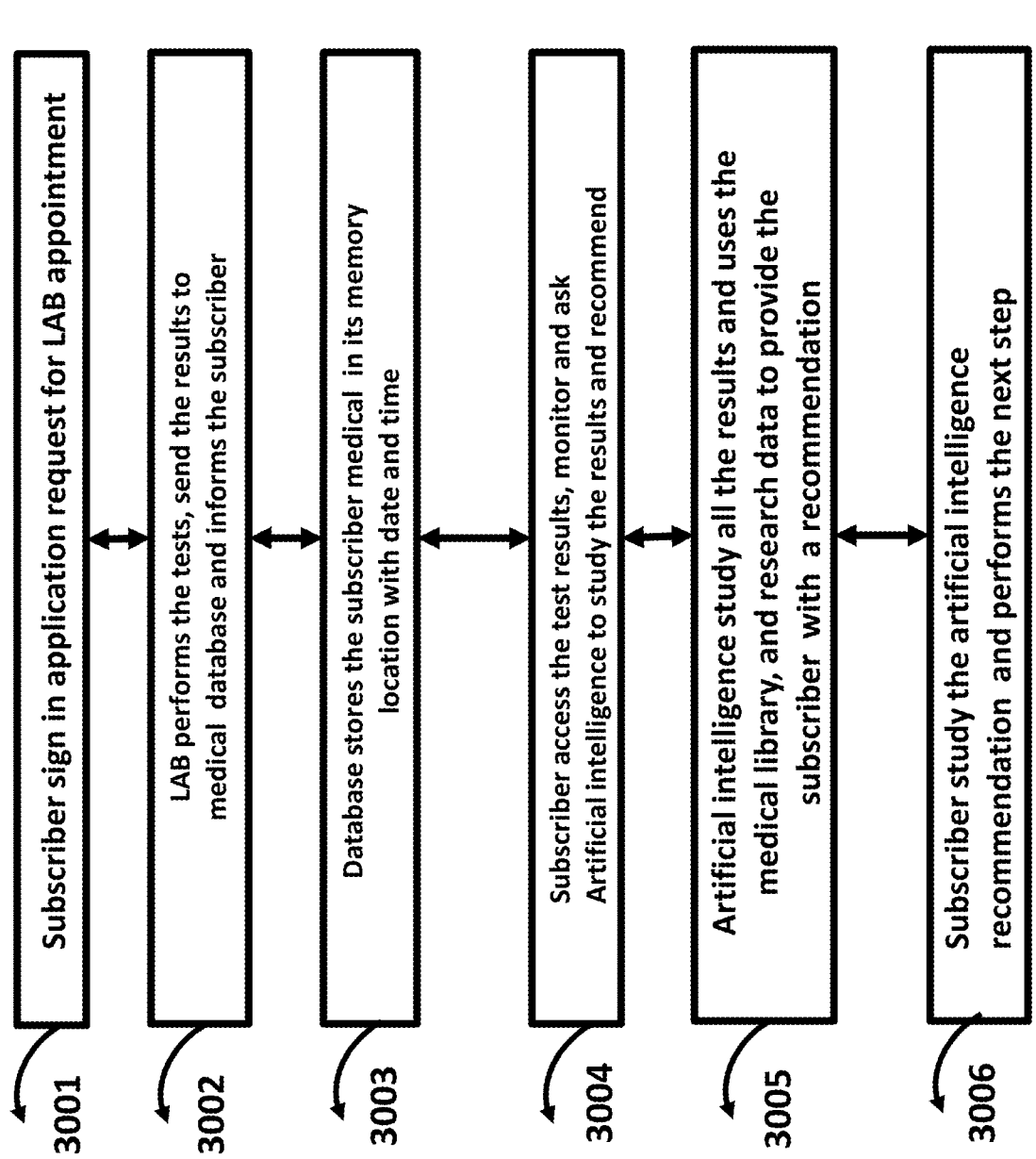

USE OF 5G IOT NETWORK FOR A VIRTUAL MEDICAL SYSTEM

The application claims priority to the following related applications and included here are as a reference.

Application: U.S. patent application Ser. No. 16/743,354 filed Jan. 15, 2020 and entitled "INTERNET OF THINGS (IOT) WITH NOVEL TIME OF DAY ACQUISITION".

Application: U.S. patent application Ser. No. 16/101,500 filed Aug. 12, 2018 and entitled "MEDICAL SYSTEM USING ARTIFICIAL INTELLIGENCE".

BACKGROUND

Across studies of population health, age nearly always stands out as the single most powerful predictor of the state of people's health and the prevailing risks of morbidity and mortality they face. The specific mechanisms that link age to health status are many and complex (World Health Organization WHO, 2015). At the biological level, ageing is associated with accumulated damage to cells that, over time, weakens the immune system, diminishes the body's capacity to repair itself and increases the risk of developing a host of different diseases. A person's age also reflects the amount of time he or she may have been exposed to various external health risks whose effects accumulate over time, such as tobacco use or unhealthy diet. Moreover, the social changes that often take place as people enter advanced ages, such as shifts in social roles and the loss of close relationships, may pose additional threats to older persons' health and well-being (WHO, 2015). However, while age is an important predictor of the average health risks people face, there is a huge degree of diversity in the health status of people at any given age, reflecting random variation across individuals, as well as differences in the life course, environment and behaviors that shape health risks. This is especially true at older ages when the risks of specific morbidities and mortality vary widely across individuals of the same age. That variability is associated with numerous other predictors of health status, including, inter alia, genetic factors, which are estimated to account for roughly a quarter of the differences in health and function observed at older ages, as well as individual characteristics such as occupation, level of income or educational attainment; environmental factors such as pollution or accessible infrastructure; and behaviors that pose risks to health, such as tobacco use, physical inactivity or excessive consumption of alcohol. Thus, while one 70-year-old person may enjoy good health that enables them to remain active in the labor force and to live without much health care support or intervention, a peer of the same age may face multiple chronic morbidities that cause significant disability and require frequent medical interventions or health care support resources.

While all older persons will eventually face declining health and functioning, their specific health trajectories may vary widely. Some older persons will experience a sudden and rapid decline from good health to death, while for others the decline in functioning will occur gradually over many years, and others still will experience periods of illness and disability interspersed by periods of partial or full recovery (WHO, 2015). The substantial heterogeneity in the health status of older persons underscores the need for health systems that are responsive to the diversity of their experience. In addition to health systems, other sectors must respond by creating the infrastructure and environments that support older persons with varying functional capacities. This includes, for example, housing and transportation infrastructure that is accessible and safe for older persons.

A recent assessment by the World Health Organization (WHO) (2015) warns that health systems around the world are falling short with respect to meeting the needs of older persons. The report summarizes the present situation:

Current public-health approaches to population ageing have clearly been ineffective. The health of older people is not keeping up with increasing longevity; marked health inequities are apparent in the health status of older people; current health systems are poorly aligned to the care that aging populations require even in high income countries; long-term care models are both inadequate and unsustainable; and physical and social environments present multiple barriers and disincentives to both health and participation.

It is safe to say that we are at the start of another industrial revolution. The rise of the connected objects known as the "Internet of Things" (IoT) will rival past technological marvels, such as the printing press, the steam engine, and electricity. From the developed world to developing world, every corner of the planet will experience profound economic resurgence. Even more remarkable is the speed with which this change will happen. A couple of decades ago there were about one billion devices connected to internet. In five year, it could be more than 50 billion.

The rise of IoT also means we are at the start of a new age of data. Two chief components of an "IoT object" are its ability to capture data via sensors and transmit data via the Internet. The declining cost of sensors since the start of the new millennium has been a main driver in the rise of IoT. In short, sensors are dirt cheap today. This has profound implications on the ability to capture data.

The Internet of Things (IoT) describes a worldwide network of intercommunicating devices. Internet of Things (IoT) has reached many different players and gained further recognition. Out of the potential Internet of Things application areas, Smart Cities (and regions), Smart Car and mobility, Smart Home and assisted living, Smart Industries, Smart health care system, Public safety, Energy & environmental protection, Agriculture and Tourism as part of a future IoT Ecosystem have acquired high attention.

The challenge is determining the prioritized hierarchy of: (1) detecting the relevant quantities, (2) monitoring and collecting the data, (3) assessing and evaluating the information, and (4) performing decision-making actions.

Fifth generation wireless systems (5G) are on the horizon and IoT is taking the center stage as devices are expected to form a major portion of this 5G network paradigm. IoT technologies such as machine to machine communication complemented with intelligent data analytics are expected to drastically change landscape of various industries. The emergence of cloud computing and its extension to fog paradigm with proliferation of intelligent 'smart' devices is expected to lead further innovation in IoT.

In order to understand what are the constituents of IoT we will need to dive into the core parts of IoT. IoT is an umbrella term combining the following 4 properties in one place:

1. People:
People are the humans using connected devices to deliver insights about their personal and professional self. This data can include interests, preferences, work, personal health etc.
2. Process:
The process is the way to ensure deliverability of right data at the right time to the right person or machine. Here data is more about insightful information or an action than just random chunk. Figuring out a way to decipher the right flow of information is a key to making the best use of big data.

3. Data:

With the increase in sources and types of data, we will also need to classify the information and analyze it to bring useful insights. Data alone is nothing but once combined with analytics and analysis this new data can help systems in decision making.

4. Things:

This is where we come across the term Internet of Things (IoT). Internet of things is the interconnectivity of devices that send and receive information data across networks like the internet. With every signal injected into the network, data is generated which needs to be collected, summarized and analyzed efficiently.

This application discloses a novel approach (virtual) to medical system using IoT network and artificial intelligence. It instantly allows patients to obtain information about their medical status and recommendations for the steps they need to take. This method eliminates a lot of steps a patient needs to take in present medical systems.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a virtual medical system uses an IoT network (fifth generation wireless system).

In another aspect, the virtual medical system consists of an application, a database and an artificial intelligence (AI).

In one aspect, the application resides on an IoT device or 5G (6G, 7G, etc.) user equipment (UE).

In another aspect, the database and AI reside on a server in a cloud.

In one aspect, the virtual medical system uses distributed IoT devices which are sensor/monitoring devices test equipment to monitor measure detect and collect information data from a human to be processed by an virtual medical system.

In another aspect, an IoT device is equipment or a tool.

In another aspect, all communication links in the IoT network are asynchronous and use Ethernet packet protocols.

In one aspect, an IoT device uses Ethernet packet protocol for over the air link between IoT network and IoT device.

In one aspect, the IoT devices use IEEE1588 (institute of electrical and electronic engineering 1588) precision time protocol (PTP) to obtain time of day.

In another aspect, the IoT device uses IEEE1588 PTP to obtain time of day from the IoT network (4G, 5G, 6G and WiFi networks).

In one aspect, an IoT device uses IEEE1588 PTP to obtain time of day from another IoT device.

In another aspect, the IoT device uses GPS (Global Positioning System) receiver to obtain location and time of day.

In another aspect, the IoT network through downlink cyclic prefix in 4G, 5G, and WiFi transmit symbol sends time of day to IoT device with nanoseconds accuracy.

In one aspect, time of day is send continuously using downlink transmit cyclic prefix.

In another aspect, the IoT network is fifth generation wireless (5G) fix and mobile data communication network.

In one aspect, the IoT network is any fix and mobile wireless data communication network beyond 5G such as sixth generation (6G), seventh generation (7G) and etc.

In one aspect, the IoT network is WiFi (wireless fidelity) network.

In one aspect, an IoT device within IoT network uses a sensor/monitoring device for certain data collection application.

In another aspect, each IoT device has an IP (internet protocol) address.

In one aspect, the IoT network uses time of day to program the IoT device an absolute time for monitoring/sensing and data collection.

In another aspect, the application within virtual medical system programs the IoT device an absolute time for monitoring/sensing and data collection.

In another aspect, the IoT network (or application) uses time of day to program the IoT devices an active time to collect data and a sleep time or idle time to save power.

In one aspect, the IoT network (or application) uses time of day to program the IoT device an absolute time to transmit collected data to the IoT network.

In one aspect, the absolute time is defined by the hour, the minute, the second, the millisecond, the microsecond, the nanosecond and the picoseconds.

In another aspect, the absolute time includes the hour.

In one aspect, the absolute time includes the hour and the minutes.

In one aspect, the absolute time includes the hour, the minutes, and the seconds.

In one aspect, the absolute time includes the hour, the minutes, the seconds, and the milliseconds.

In one aspect, the absolute time includes the hour, the minutes, the seconds, the milliseconds, and the microseconds.

In one aspect, the absolute time includes the hour, the minutes, the seconds, the milliseconds, the microseconds, and the nanoseconds.

In one aspect, the IoT network (AI or application) defines the date and time of day for data collection by an IoT device.

In one aspect, the IoT network (AI or application) specifies the date and absolute time an IoT device sends the collected data to the IoT network for storage or study and analysis.

In another aspect, the IoT network (AI or application) demands the IoT device to send the data real time.

In one aspect, an IoT device comprises of a sensor/monitoring device and a wireless transceiver to communicate with IoT network as well as other IoT devices or UE.

In another aspect, the information data obtained by IoT devices is used for specified application.

In another aspect, the information data obtained by IoT devices is used for any application.

In one aspect, the information data sent by IoT devices depends on the sensors/monitoring device that is used.

In another aspect, the IoT device obtains time of day at start up.

In another aspect, the start and end time of communication and data collection of IoT device is defined by the IoT network (application).

In another aspect, the IoT devices use Ethernet packet protocol to communicate.

In one aspect, the IoT devices use a proprietary packet protocol to communicate.

In one aspect, the IoT devices use a WiFi protocol to communicate.

In another aspect, the IoT devices support at least one of a BLUETOOTH transceiver, a ZIGBEE transceiver, an Infrared transceiver, and a WiFI transceiver.

In another aspect, the IoT device is a biometric device.

In one aspect, an IoT device is any equipment used in a hospital.

In another aspect, an IoT device is any wearable device.

In another aspect, an IoT device is in general any equipment and tool within virtual medical system.

In one aspect, the IoT device has at least one sensor/monitoring device to collect data.

In one aspect, the type of IoT device is identified by its IP address.

In another aspect, the type of IoT device is identified by its type indicator.

In another aspect, the type of IoT device is identified by its serial number.

In another aspect, the IoT device sends a time stamp with its information data that shows time of day.

In one aspect, the application which is resides on UE (IoT device) receives information data from IoT devices that are attached to a patients, analyses them and then sends them to be stored in database on a server in a cloud.

In another aspect, the application after receiving the information data from IoT devices that are attached to patient sends them raw to the database for storage.

In one aspect, the IoT devices that are attached to a patient send the information data directly to the database to be stored.

In another aspect, the AI receives the information data collected by the IoT devices that are connected to the patient through the application which resides on UE (IoT device) used by the patient.

In one aspect, the AI receives the information data collected by IoT devices that are connected to the patient directly from the IoT devices.

In one aspect, the AI receives the information data collected by IoT devices that are connected to the patient directly and real-time from the IoT devices.

In another aspect, the patient uses the application which resides on UE (IoT device) to activate the AI and send medical status and symptoms.

In one aspect, the patient and the AI communicate interactively through the application which resides on UE (IoT device).

In another aspect, the patient arranges with a mobile test laboratory (LAB) to visit at a location defined by the patient to perform various blood, urine, stool, and imaging tests.

In one aspect, the patient arranges with mobile test LAB to perform the test at patient's home.

In another aspect, the mobile test LAB sends the results to the patient through the application which resides on patient's UE (IoT device).

In one aspect, the patient after receiving the test results from mobile LAB sends them to the database in the cloud to be stored.

In another aspect, the mobile LAB directly sends the patient's test results to the database in the cloud to be stored.

In another aspect, the patient arranges with a stationary test laboratory (LAB) to visit and perform various blood, urine, stool, and imaging tests.

In another aspect, the stationary test LAB sends the test results to the patient through application which resides on patient's UE (IoT device).

In one aspect, the patient after receiving the test results from stationary test LAB sends them to the database in the cloud to be stored.

In another aspect, the stationary LAB directly sends the patient's test results to the database in the cloud to be stored.

In one aspect, all components of the virtual medical system exchange information data in form of a text, a graph, a recorded audio, an image, a recorded video, and other means.

In another aspect, the information data is stored in the database in form of a text, a graph, a recorded audio, an image, a recorded video, and other means.

In one aspect, the information data is stored in a database with detail information (name, data of birth, identification number, driving license, social security number, immigration status, address, phone number, email address, insurance information and if required photo) of the patients.

In another aspect, the information data stored in database includes stationary test LAB identification, mobile test LAB identification and biometric device (IoT device) identification information.

In one aspect, the identification information includes name, address, phone number, and website.

In one aspect, the patient, the AI, the ER (emergency room), the EMS (emergency medical services), the doctors, and the hospitals have access to patient medical information data stored in database on a server in a cloud.

In another aspect, the patient through the application activates the AI and sends to the AI the patient's medical status and symptoms.

In one aspect, the AI reviews patient's medical status and symptom then retrieves patient's medical information data that is stored in the database and if needed communicates with the patient for more information.

In another aspect, the AI studies all the medical information data obtained and then consult a medical library that is stored in the database on a server in a cloud. The AI may communicate more with the patient for more information during process of studying the medical information data and consulting medical library.

In one aspect, the AI after concluding study of the medical information data and consultation with the medical library makes a decision.

In another aspect, the AI's decision identifies if the case is life threatening, EMS (emergency medical services), ER (emergency room) or outpatient. For life threatening case AI calls 911 and provides detail information of the patient. The AI in case of EMS calls a local facility and provides them with detail information of patient to dispatch suitable resource to deal with the patient situation. The AI in case of ER provides detail information of a local ER to the patient to visit.

In one aspect, when the patient's case is outpatient the AI determines if the patient needs to see a doctor in person or have a video call with a doctor and then arranges for the patient a visit to a doctor in person or a video call with a doctor.

In another aspect, the AI determines if the patient requires seeing a specialist and then arranges a visit with a specialist and sends detail medical record of the patient to the specialist for the visit.

In one aspect, in all other cases of outpatient the AI provides appropriate recommendation, prescription and various lab and imaging tests.

In another aspect, the patient at the end of treatment will have all tests, treatments, prescriptions and results recorded in database and follows up with the AI.

In one aspect, all components of virtual medical system using 4G, 5G or WiFi network are time synchronized and have the same time of day.

BRIEF DESCRIPTION OF THE DRAWINGS

FIGS. 11A through 11K depict an AI algorithm FIG. 12 depicts a method used by virtual medical system The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
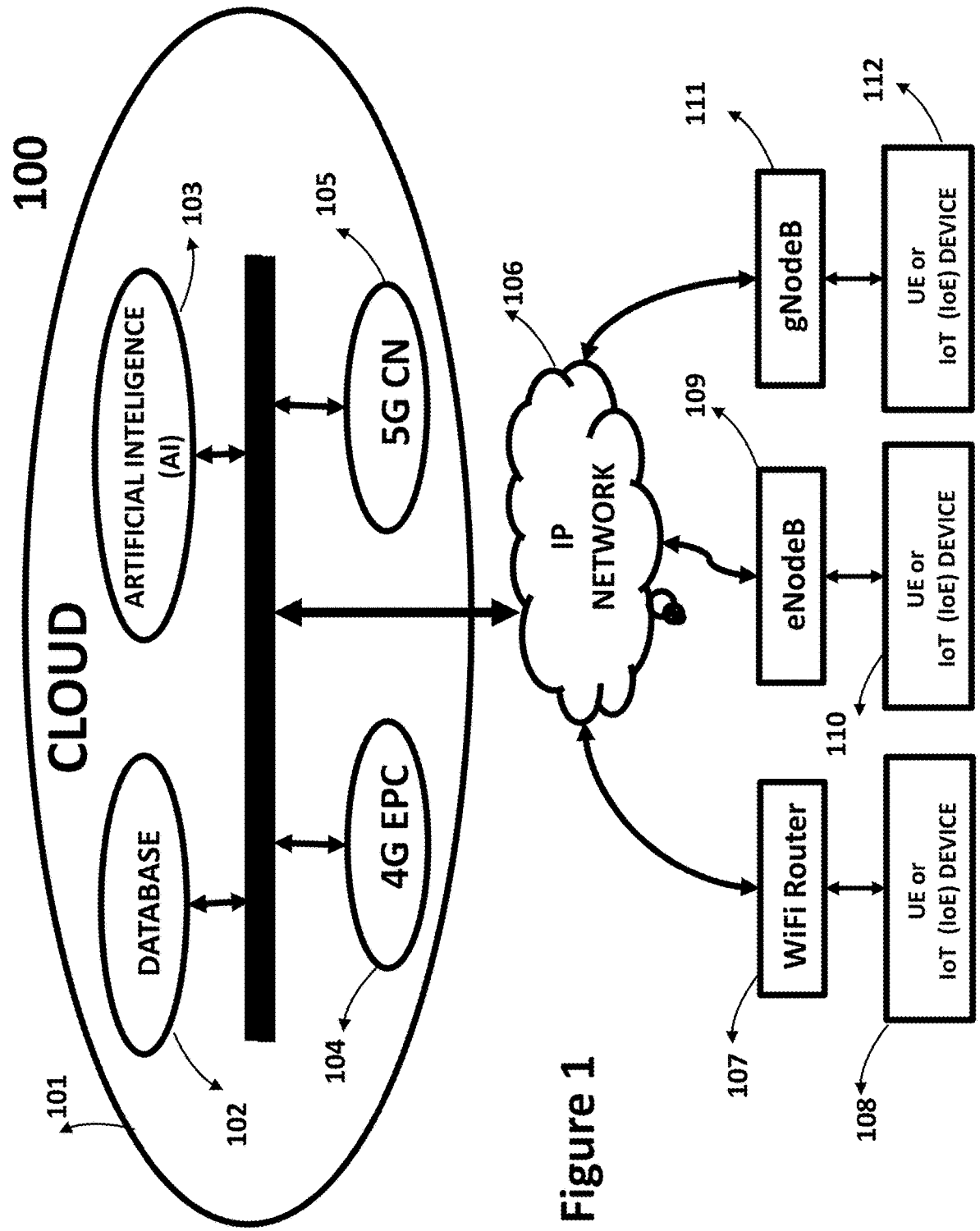
FIG. 1 illustrates 4G, 5G, and WiFi IoT Network

FIG. 1 depicts 4G, 5G and WiFi (wireless fidelity) end to end IoT networks 100 used by a virtual medical system. 4G network facilitates communication between user equipment (UE) or IoT device 110 and evolved packet core (EPC) 104 through evolved node B (eNodeB) 109 and IP (Internet protocol) network 106. 5G network facilitates communication between user equipment (UE) or IoT device 112 and core network (CN) 105 through next generation Node B (gNodeB) 111 and IP network 106. WiFi network facilitates communication between user equipment (UE) or IoT device 108 and the cloud 101 through WiFi router 107, and IP network 106. UEs 108, 110 and 112 also act as IoT device. Cloud 101 accommodates EPC 104 and CN 105 as well as database 102 and artificial intelligence 103 and allows UEs or IoT devices 108, 110 and 112 have access to database 102 and artificial intelligence (AI) 103.

In 4G, 5G (6G, 7G, etc.) and WiFi networks there is a need for synchronization. There are a number of synchronization techniques that are used in data communication networks and the most common one depending on requirements of network components or ports are syncE, PTP or IEEE1588, NTP, and GPS. The Network Time Protocol (NTP) is a networking protocol for clock synchronization between computer systems over packet-switched, variable-latency data networks. In operation since before 1985, NTP is one of the oldest Internet protocols in current use. Synchronous Ethernet, also referred to as SyncE, is an ITU-T standard for computer networking that facilitates the transference of clock signals over the Ethernet physical layer. This signal can then be made traceable to an external clock. IEEE 1588 Precision Time Protocol (PTP) is a packet-based two-way communications protocol specifically designed to precisely synchronize distributed clocks to sub-microsecond resolution, typically on an Ethernet or IP-based network. Global Satellite Positioning System (GPS) signal is received, processed by a local master clock, time server, or primary reference, and passed on to "slaves" and other devices, systems, or networks so their "local clocks" are likewise synchronized to coordinated universal time (UTC).

In 4G, 5G and WiFi network 100 when the link between two network component ports is Ethernet then there is a need to synchronize the two network components using SyncE, IEEE1588 (PTP) or NTP depending on requirements and specification of two network components.

Mobile user equipments (UE) or IoT devices 108, 110, and 112 use GPS to obtain time of day/location and over the air protocol to achieve frequency and phase synchronization. However, for UEs or IoT devices that either can't see the GPS satellites, GPS signal is very weak, or GPS receiver increases cost, size, and power consumption another technique to acquire time of day is require. UEs and IoT devices can use their received 4G, 5G and WiFi signal to achieve frequency and phase synchronization. UEs and IoT devices that do not have access to GPS signal can either obtain time of day from UEs and IoT devices in surrounding environment that have access to GPS signal and are accessible or obtain it from eNodeB, gNodeB and WiFi router that they communicate with.

There are three techniques that UEs and IoT devices can use to obtain time of day from eNodeB, gNodeB and WiFi router. The precision of time of day will be different using these three techniques. Time of day with different accuracies is used for different applications. The less accurate time of day uses one way communication between eNodeB, gNodeB and WiFi router and UEs or IoT devices 108, 110, and 112, and the more accurate time of day uses two way communications between eNodeB, gNodeB and WiFi router and UEs or IoT devices 108, 110, and 112. In all methods eNodeB, gNodeB and WiFi router should have time of day. In 4G, 5G and WiFi network 100 for architectures that eNodeB, gNodeB and WiFi router do not have time of day or can't support exchange of time of day with UEs and IoT devices then the network component prior to eNodeB, gNodeB and WiFi router can be used to propagate time of day to UEs and IoT devices 108, 110, and 112.

In one embodiment, 4G, 5G and WiFi network 100 provide time of day to UEs and IoT devices, using institute of electrical and electronic engineering (IEEE1588) precision time protocol (PTP). IEEE1588 PTP exchanges the timing messages to and from UEs or IoT devices 108, 110, and 112 and one infrastructure component of 4G, 5G and WiFi network 100.

In one embodiment, IEEE1588 PTP messages are exchanged between UEs or IoT devices 108, 110, and 112 and eNodeB, gNodeB and WiFi router.

In another embodiment, IEEE1588 PTP messages are exchanged between UEs or IoT devices 108, 110, and 112 and cloud 101 or IP network 106.

In one embodiment of 4G, 5G and WiFi network 100, time of day is sent to UEs and IoT devices 108, 110, and 112 by cyclic prefix of OFDM (orthogonal frequency division multiplexing) symbols from eNodeB, gNodeB and WiFi router where IFFT (inverse fast Fourier Transform) is performed.

In one embodiment, 4G, 5G and WiFi network 100 utilizes unused downlink sub-carriers to send time of day to UEs or IoT devices 108, 110, and 112.

In another embodiment, 4G, 5G and WiFi network 100 utilizes unused bits or messages in various downlink channels to send time of day to UEs or IoT devices 108, 110, and 112.

In one embodiment, all components of 4G, 5G and WiFi network 100 are time synchronized and have the same time of day.

In one embodiment, 5G, 6G, and 7G networks transmit Ethernet packets over the air to UEs or IoT devices 108, 110, and 112 in order to have an end-to-end network using a single packet protocol. By doing this both hardware and software is significantly simplified.

In another embodiment, UEs and IoT devices 108, 110, and 112 obtain time of day from other UEs or IoT devices in surrounding environment that are in their communication range and have time of day.

In one embodiment, UEs and IoTs devices 108, 110, and 112 use another frequency to communicate with other UEs and IoT devices in surrounding environment and exchange broadcast data.

In another embodiment, UEs and IoT devices 108, 110, and 112 communicate with other UEs and IoT devices by exchanging Ethernet packets or any other proprietary packets.

In one embodiment, UEs and IoT devices 108, 110, and 112 use similar physical layer as 4G, 5G or WiFi to communicate with or broadcast their information data to other UEs and IoT devices in their surrounding environment without introducing any unwanted interference.

In another embodiment, UEs and IoT devices 108, 110, and 112 use a physical layer different from 4G, 5G and WiFi to communicate with or broadcast their information data to other UEs and IoT devices in their surrounding environment without introducing any unwanted interference.

In another embodiment, a specific time is defined and communicated to UEs and IoT devices 108, 110, and 112 by 4G, 5G and WiFi networks for broadcasting or communicating with other UEs or IoT devices in order to avoid interruption and interference.

In one embodiment, UEs and IoT devices 108, 110, and 112 support Bluetooth, Zigbee, infrared, WiFi, and any other wireless communication systems to communicate with other UEs and IoT devices in their surrounding environment and exchange information data and transmit and receive broadcast data. The communication between UE and IoTs devices is encrypted and highly secured.

In another embodiment, UEs and IoT devices transmit and receive broadcast data that includes the type of UE and IoT device, their IP address, their location, their mass, time of day, method of obtaining time of day (IEEE1588, cyclic prefix, GPS, or other methods).

In one embodiment, UEs or IoT devices broadcast time of day at their transmitter antenna port to other UEs or IoT devices in their surrounding environment.

In one embodiment, UEs and IoT devices 108, 110, and 112 support WiFi, Bluetooth, Zigbee over the air wireless protocols.

Figure 2:
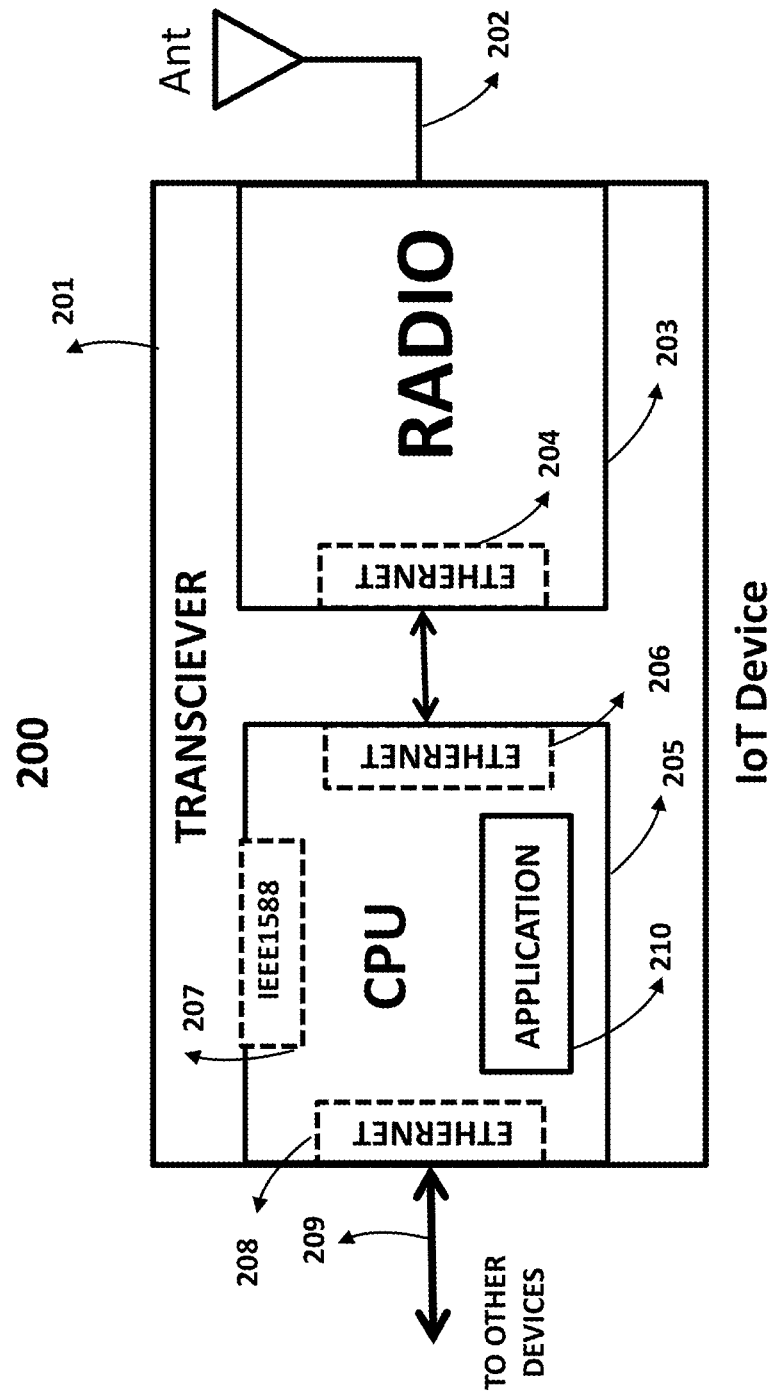
FIG. 2 illustrates a typical IoT device that communicates with WiFi, 4G and 5G networks

FIG. 2 illustrates the architecture of an IoT device (UE) 200. In general IoT device (UE) 200 communicates with 4G, 5G and WiFi networks to exchange information data. IoT device (UE) 200 through radio 203 attaches itself to a 4G, 5G (6G, 7G, etc.) or WiFi network in its surrounding environment and listens to commands to perform certain functions. Radio 203 when receives a command sends it to CPU 205 to be evaluated and performed by CPU 205 (application 210) or uses other devices that are connected to CPU 205 to perform the command or commands. Then the results obtained from performing the commands through CPU 205 (application 210) and radio 203 is transmitted to 4G, 5G or WiFi network for analysis and storage. CPU 205 also accommodates application 210 that communicates with database 102, AI 103, or external devices connected to IoT device (UE) 200. Application 210 is activated by an operator of IoT device (UE) 200 and communicates with external devices attached to IoT device (UE) 200 through CPU 205, interface 208 and link 209. Application 210 also communicate with database 102 and AI 103 through CPU 205, radio 203, antenna 202 using one of 4G, 5G or WiFi network.

In one embodiment, IoT device (UE) 200 includes among other things transceiver 201 which consists of antenna 202, radio 203, possible radio Ethernet port 204, CPU 205, application 210, possible Ethernet port 206 towards radio, possible IEEE1588 PTP 207, and Ethernet port 208 towards other devices.

In one embodiment, IoT device (UE) 200 through antenna 202 and radio 203 attaches to 4G, 5G, or WiFi network and if needed obtains time of day.

In another embodiment of IoT device (UE) 200, transceiver 201 obtains time of day through IEEE1588 PTP, downlink transmit cyclic prefix, downlink transmit unused sub-carriers, or unused bits or messages in one of downlink channels from 4G, 5G or WiFi network.

In one embodiment, IoT device (UE) 200 communicates via its transceiver's CPU 205 with another device using an Ethernet port 208 and link 209.

In another embodiment, IoT device (UE) 200 propagates time of day to an external device or equipment via its transceiver's Ethernet port 208 and link 209 using IEEE1588 PTP 207. This way IoT device (UE) 200, devices connected to IoT device (UE) 200, cloud 101, database 102, AI 103, 4G network 100, 5G network 100, and WiFi network 100 are all time synchronized and have the same time of day.

In one embodiment, IoT device (UE) 200 receives commands or information data from 4G, 5G or WiFi network and communicates the commands or information data to application 210 though CPU 205 or an external device through its transceiver's Ethernet port 208 and link 209.

In one embodiment, IoT device (UE) 200 receives information data from an external device through its Ethernet port 208 and sends it to application 210 or transmits it to 4G, 5G or WiFi network using its transceiver's CPU 205, radio 203 and antenna 202.

In another embodiment, IoT device (UE) 200 communicates with an external device and exchange time of day as well as information data and commands via its transceiver's CPU 205 using a serial interfaces or a parallel interface instead of Ethernet interface 208.

In one embodiment, IoT device (UE) 200 communicates with other IoT devices and exchange broadcast data. The IoT device (UE) 200 uses a different frequency or channel to communicate with another IoT device in order to avoid interruption and interference.

In another embodiment, IoT device (UE) 200 communicates with other IoT devices in its surrounding environment that are in its communication range using a proprietary physical layer or a physical layer similar to 4G, 5G or WiFi.

In one embodiment, IoT device (UE) 200 exchanges Ethernet packets or any other proprietary packets with other IoT devices in its surrounding environment.

In another embodiment, IoT device (UE) 200 communicates with a WiFi network in its surrounding environment.

In one embodiment, IoT device (UE) 200 through its transceiver 201 supports WiFi, Bluetooth, Zigbee over the air wireless protocols.

In one embodiment, IoT device (UE) 200 exchange IEEE1588 PTP messages with another IoT device or a WiFi router in surrounding environment to obtain or propagate time of day.

In another embodiment of IoT device (UE) 200, the device that is connected to transceiver 201 through link 209 is any device or object that is remotely controlled to perform certain function.

In one embodiment of IoT device (UE) 200, application 210 through transceiver 201 communicates with AI 103 and exchanges information data.

In one embodiment of IoT device (UE) 200, application 210 through transceiver 201 accesses database 102 to retrieve or store medical information data.

In one embodiment of IoT device (UE) 200, application 210 through transceiver link 209 configures an external device to perform certain function real time or at specific time.

In one embodiment of IoT device (UE) 200, application 210 through transceiver link 209 retrieves information data from an external device in real time or at specific time.

In one embodiment of IoT device (UE) 200, application 210 through transceiver 201 and link 209 arranges for AI 103 to monitor an external device information data.

In one embodiment of IoT device (UE) 200, application 210 through transceiver 201 and link 209 arranges for AI 103 to retrieve information data directly from an external device connected to transceiver 201 real-time or at specific time.

In one embodiment of IoT device (UE) 200, application 210 through transceiver 201 and link 209 arranges for database 102 to retrieve information data directly from an external device connected to transceiver 201 real-time or at specific time.

In one embodiment of IoT device (UE) 200, application 210 through transceiver 201 and link 209 arranges for an external device to store its information data to database 102 real-time or at specific time.

In one embodiment of IoT device (UE) 200, application 210 through transceiver 201 and link 209 retrieves information data collected by an external device and sends them through CPU 205, radio 203, and antenna 202 to database 102 to be stored.

In one embodiment of IoT device (UE) 200, application 210 through transceiver 201 and link 209 retrieves information data collected by an external device, analyses them and then sends them through CPU 205, radio 203, and antenna 202 to database 102 to be stored.

In another embodiment, IoT device (UE) 200 communicates with an external device through link 209 which is wireless.

In another embodiment, IoT device (UE) 200 communicates with an external device through its radio 203 and antenna 202 using 4G, 5G, WiFi or a proprietary air protocol.

In another embodiment, IoT device (UE) 200 communicates with an external device through Zigbee, Bluetooth or a proprietary wireless radio embedded in transceiver 201.

Figure 3:
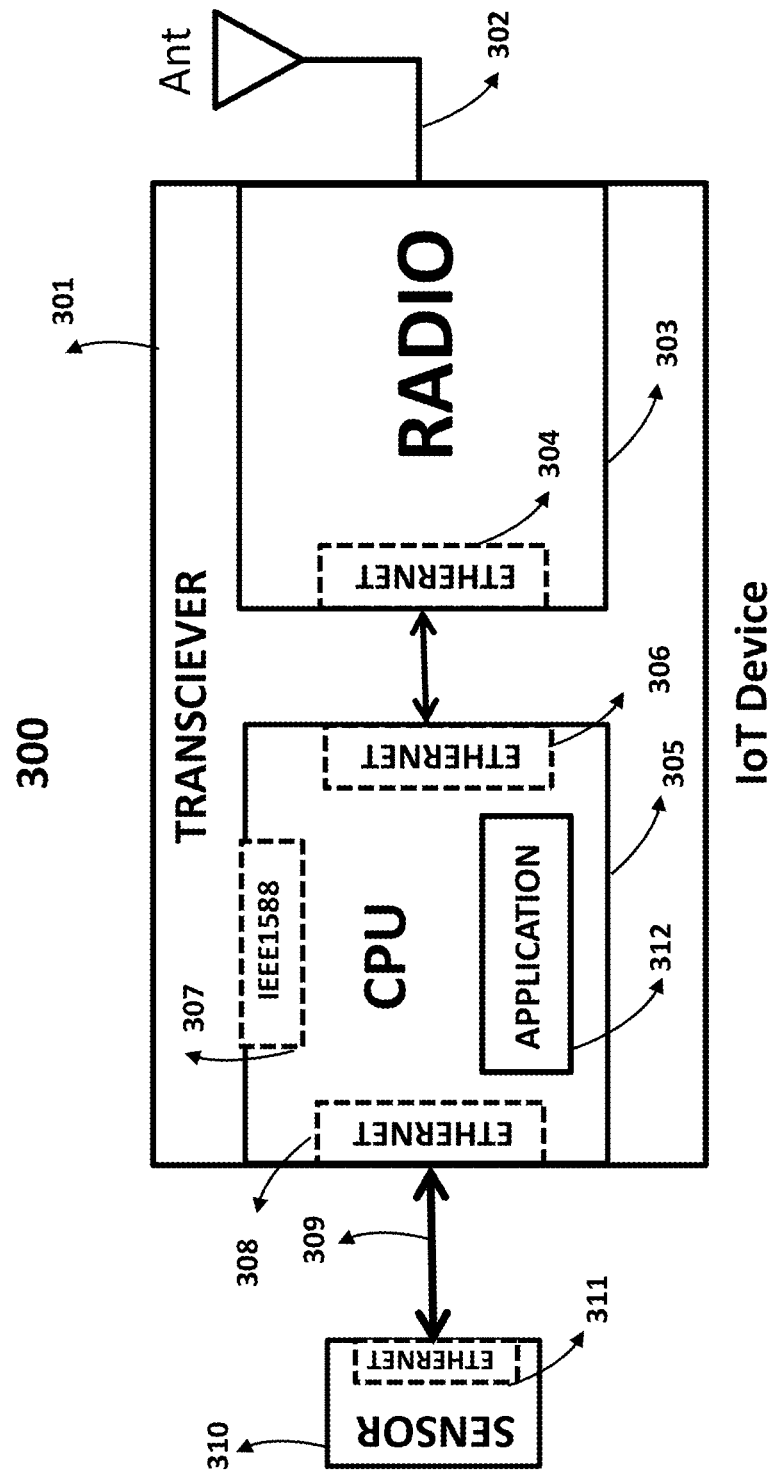
FIG. 3 illustrates a typical IoT device that communicates with WiFi, 4G and 5G networks supporting a single sensor or external device

FIG. 3 shows the architecture of an IoT (UE) sensor device 300. In general IoT (UE) sensor device 300 communicates with 4G, 5G and WiFi networks to exchange information data. IoT (UE) sensor device 300 through radio 303 attaches itself to a 4G, 5G or WiFi network in its surrounding environment and listens to commands to activate sensor 310. Radio 303 when receives a command, sends it to CPU 305 to be evaluated and performed by CPU 305 (application 312) or sensor 310 that is connected to CPU 305. Then the results obtained from performing the commands through CPU 305 and radio 303 is transmitted to 4G, 5G or WiFi network for storage or analysis.

In one embodiment, IoT (UE) sensor device 300 includes, among other things transceiver 301 which consists of antenna 302, radio 303, possible radio Ethernet port 304, CPU 305, Application 312, possible Ethernet port 306 towards radio, possible IEEE1588 PTP 307, possible Ethernet port 308 and sensor 310 with possible Ethernet port 311.

In one embodiment, IoT (UE) sensor device 300 uses an attached external device or sensor 310.

In another embodiment, IoT (UE) sensor device 300 uses an external device which is a sensor 310.

In one embodiment, IoT (UE) sensor device 300 uses an external sensor 310 that communicates with transceiver 301 using Ethernet packet protocol through Ethernet ports 311 and 308.

In another embodiment, the link 309 between Ethernet port 308 of transceiver 301 and Ethernet port 311 of sensor 310 is a wired link or a wireless link.

In another embodiment of IoT (UE) sensor device 300, the wire link 309 is a standard serial interface, a proprietary serial interface, or a parallel interface.

In one embodiment of IoT (UE) sensor device 300, the wireless link 309 between transceiver 301 and sensor 310 is at least one of Bluetooth, Zigbee, Infrared, WiFi, or any proprietary wireless link.

In another embodiment of IoT (UE) sensor device 300, the sensor 310 does not necessarily sense anything. Sensor 310 is a tool, equipment, a robot hand, an on/off switch, any activation or deactivation device, biometric device, and any device, equipment or object that is remotely controlled to perform certain function. The function is monitoring, collecting information data and any other function that can be performed by sensor 310.

Figure 4:
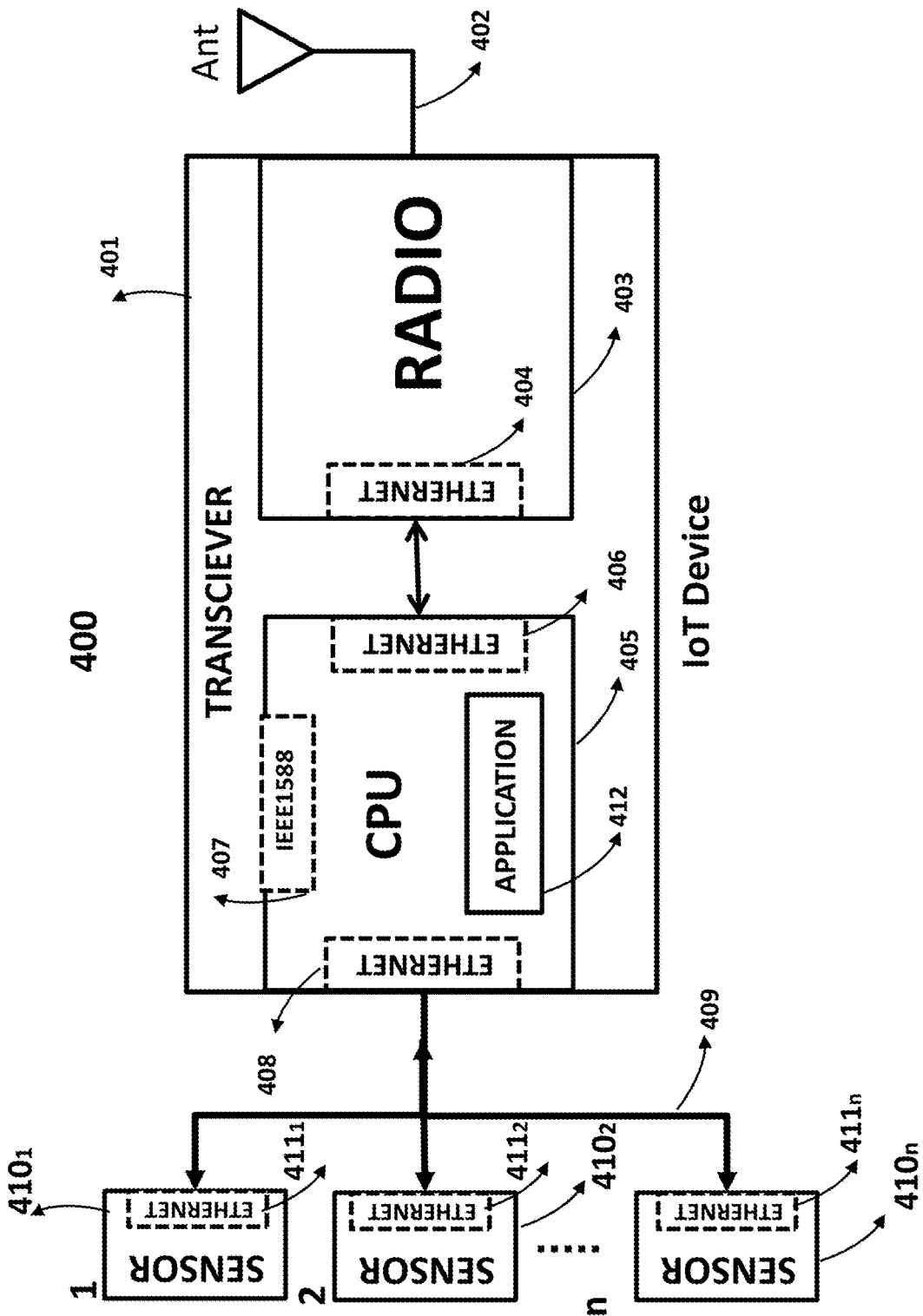
FIG. 4 depicts a typical IoT device that communicates with WiFi, 4G and 5G networks and supports multiple sensors and external devices

FIG. 4 shows the architecture of an IoT (UE) sensor network 400. In general IoT sensor (external device) network 400 communicates with 4G, 5G, and WiFi networks to exchange information data. IoT (UE) sensor (external device) network 400 through radio 403 attaches itself to a 4G, 5G (6G, 7G) or WiFi network in its surrounding environment that supports Internet of Things and listens to commands to activate or monitor sensor (external device) network $410_1$ to $410_n$. Radio 403 when receives a command from (application 412, 4G, 5G, or WiFi network), sends it to CPU 405 to be evaluated and performed by CPU 405 or sensor (external device) network $410_1$ to $410_n$ that is connected to transceiver 401. Then the results obtained from performing the commands through CPU 405 and radio 403 is transmitted to 4G, 5G or WiFi network for storage and analysis. Application 412 also (through CPU 405) receives the results (information data) from sensors (external devices) network $410_1$ to $410_n$ and if needed through CPU 405 and radio 403 transmits them to 4G, 5G or WiFi network for storage and analysis.

In one embodiment, IoT (UE) sensor (external device) network 400 includes among other things transceiver 401 which consists of antenna 402 (possible embedded local artificial intelligence), radio 403, possible radio Ethernet port 404, CPU 405, application 412, possible Ethernet port 406 towards radio, possible IEEE1588 PTP 407, possible Ethernet port 408 and sensor (external device) network $410_1$ to $410_n$.

In another embodiment, IoT (UE) sensor (external device) network 400 uses an external monitoring sensor (external device) network $410_1$ to $410_n$ that can perform various functions autonomously or through commands that sent to it remotely.

In one embodiment, IoT (UE) sensor (external device) network 400 uses an external sensor (external device) network $410_1$ to $410_n$ that communicates with transceiver 401 through Ethernet ports $411_1$ to $411_n$.

In another embodiment, sensor (external device) network $410_1$ to $410_n$ can be a monitoring network $410_1$ to $410_n$ or a mix of sensors, monitoring devices, autonomous devices, and remotely controlled devices or equipments.

In one embodiment, each device within network of devices $410_1$ to $410_n$ has an IP (internet protocol) address that identifies the device.

In another embodiment, each device within network of devices $410_1$ to $410_n$ uses its serial number for its identity.

In one embodiment of IoT (UE) sensor (external device) network 400, at least one of an Ethernet packet protocol and a proprietary packet protocol is used for communication between transceiver 401 and devices/equipment $410_1$ to $410_n$.

In another embodiment, link 409 between Ethernet port 408 or port 408 of transceiver 401 and Ethernet ports $411_1$ to $411_n$ or ports $411_1$ to $411_n$ of devices $410_1$ to $410_n$ is a wired link, a wireless link or a mix of wired and wireless.

In another embodiment of IoT (UE) sensor (external device) network 400, wired link 409 is a standard serial interface, a proprietary serial interface, or a parallel interface.

In one embodiment of IoT (UE) sensor (external device) network 400, wireless link 409 between transceiver 401 and devices $410_1$ to $410_n$ is at least one of Bluetooth, Zigbee, Infrared, WiFi, or any proprietary wireless link.

In one embodiment, IoT (UE) sensor (external device) network 400 receives an absolute time at least from one of application 412, 4G network, 5G network, and WiFi network for its various activities as well as scheduling activities of the external devices connected to IoT (UE) sensor (external device) network 400.

In another embodiment of IoT (UE) sensor (external device) network 400, application 412 individually configures devices $410_1$ to $410_n$ based on their application.

In another embodiment of IoT (UE) sensor (external device) network 400, application 412 collects information data from individual devices $410_1$ to $410_n$ and analyzes them to be displayed by transceiver 401 or sent to database 102 to be stored.

In another embodiment of IoT (UE) sensor (external device) network 400, application 412 collects information data from devices $410_1$ to $410_n$ in real-time or at specific time.

In another embodiment of IoT (UE) sensor (external device) network 400, application 412 configures devices $410_1$ to $410_n$ to collect information data real-time or at specific time.

In another embodiment of IoT (UE) sensor (external device) network 400, application 412 configures devices $410_1$ to $410_n$ to directly update database 102 real-time or at specific time with the information data that is collected.

In one embodiment of IoT (UE) sensor (external device) network 400, function of AI 103 is embedded with application 412 in CPU 405 as a local artificial intelligence 103.

In another embodiment of IoT (UE) sensor (external device) network 400, application 412 configures devices $410_1$ to $410_n$ to be monitored by AI 103 (or local AI) real-time or at specific time.

In one embodiment of IoT (UE) sensor (external device) network 400, application 412 configures the operating parameters of devices $410_1$ to $410_n$.

Figure 5:
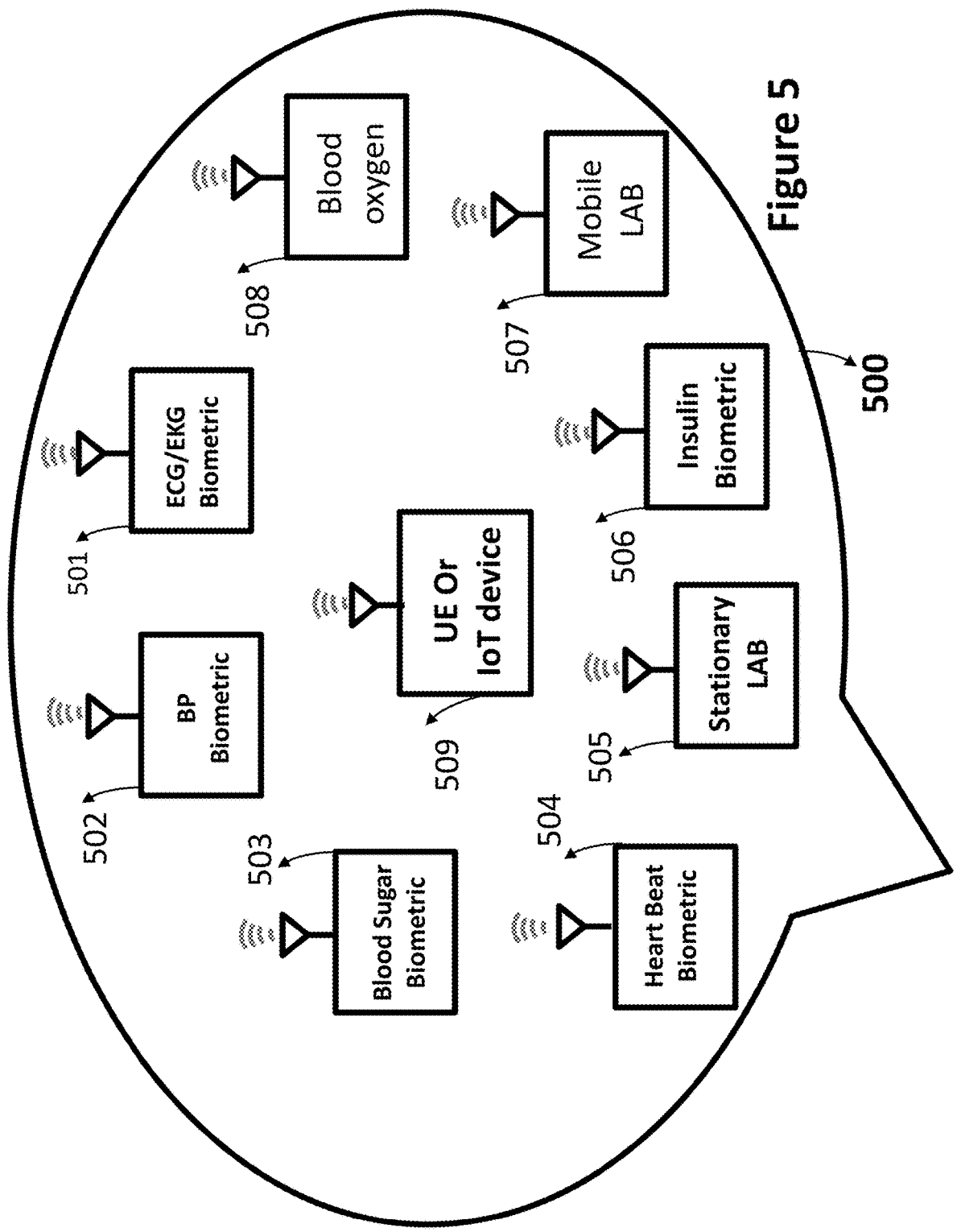
FIG. 5 shows typical biometric devices (sensors) that communicate with an IoT device or user equipment (UE)

FIG. 5 depicts typical devices (equipment) 500 that are used for medical purposes and communicate with an IoT (UE) device (200, 300, 400). In general devices (equipment) 500 provide information data of a patient to be used by patient, a doctor, AI 103, a test laboratory and stored in database 102. Devices (equipment) 500 are of three types, attachable (wearable) to the patient, stationary, and mobile. The attachable (wearable) devices (equipment) that also called biometric devices are attached to the body of the patient and configured by the IoT (UE) device through an application to collect information data real-time or at specific time and transmit the information to the IoT (UE) device used by patient (through application), database 102 for storage, a doctor, or AI 103.

Devices (equipment) 500 includes, among other things, stationary LAB 505, mobile LAB 507, ECG/EKG biometric 501, blood pressure biometric 502, blood sugar biometric 503, heart beat biometric 504, insulin biometric 506 and blood oxygen biometric 508 and any other biometric medical devices used by a patient. Al these devices and equipment communicate with IoT (UE) device 509. They can also directly communicate with database 102, AI 103, or doctors. Devices 501 to 508 can have their own IP address and act as an IoT device and communicate through WiFi, 4G, or 5G network to other entities like database 102, AI 103 or doctors and medical centers (hospitals, clinics, ambulances, ER, EMS and others).

In one embodiment, when biometric devices act as an IoT device they can communicate among themselves and exchange information data. AI communications are encrypted and highly secured.

Figure 6:
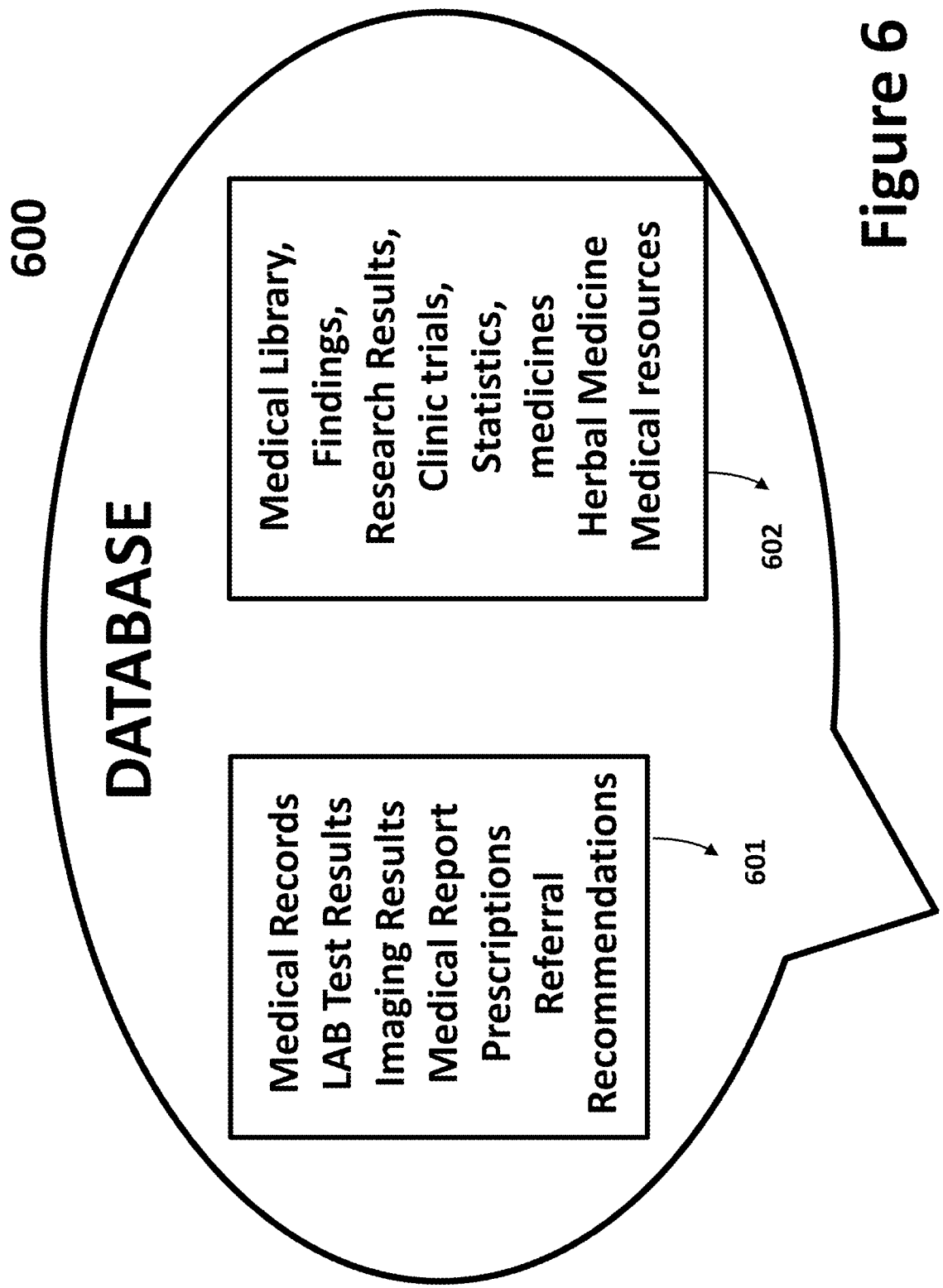
FIG. 6 illustrates two key databases used by virtual medical system

FIG. 6 shows database 600. Database 600 is home to medical record database 601 and medical library database 602. In general database 601 stores medical record of various patients and database 602 stores all medical literature (findings, research results, statistics, traditional treatment, western treatments, surgeries, and any other information that helps diagnostic and method of treatments) and resources. Resources includes detail information (name, address, phone number, license number, website, services, ratings, and cost) and their specialty, clinics and their services, hospitals and their services, ER, EMS, laboratories and their services, biometric devices and their functions and parameters, drug stores and their addresses, herbal drugs and their cost and benefits, chemical drugs and their cost, benefit and prevention. Both medical record database 601 and medical library 602 can be accessed by AI 103, application 210 (312, 412), and stationary and mobile LABs as well as biometric devices (501 to 508).

Figure 7:
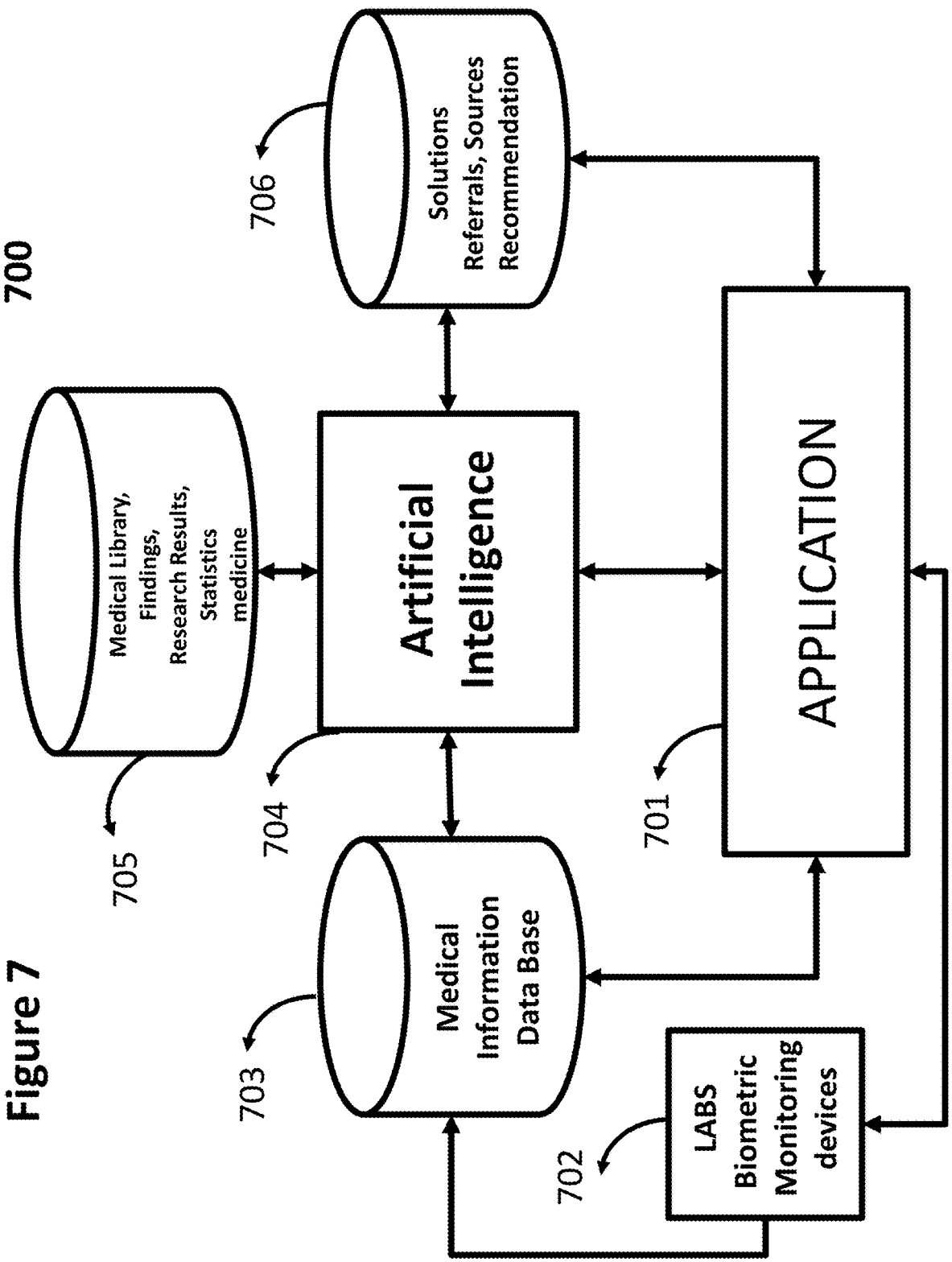
FIG. 7 depicts a virtual medical system using artificial intelligence

FIG. 7 illustrates an embodiment of a virtual medical system using artificial intelligence (VMAI) 700. In general, the VMAI 700 provides medical recommendation to a patient based on the patient's medical information data. The patient through application 701 embedded in IoT (UE) device 200 communicates with medical (biometric) monitoring devices/LABs 702 ($410_1$ to $410_n$), a medical information database 703 (102), an artificial intelligence (AI) 704 (103), and a solution and sources recommendation 705. The patient through application 701 (210, 312, 412) controls the medical (biometric) monitoring devices ($410_1$ to $410_n$) that are attached to IoT (UE) device 200 and makes various appointments with different test laboratories (stationary or mobile, $410_1$ to $410_n$) to perform various tests on the patient and sends the results from biometric monitoring devices and the test laboratories (Labs) to the medical information database 703 (102) for storage. The patient through application 701 (210, 312, 412) based on his or her medical status and condition contacts AI 704 (103) for recommendation and solutions. The patient also through application 701 (210, 312, 412) accesses the test results stored in the medical information database 703 (102) and based on the results asks the artificial intelligence (AI) 704 (103) for recommendation. Artificial intelligence (AI) 704 (103) uses the patient's test results stored in medical information database 703 (102) and the patient's inputs from application 701 (210, 312, 412) and through medical library, findings and research results database 705 (102) provides recommendations for solutions and sources in solution and sources recommendation 706. The patient through application 701 (210, 312, 412) accesses the recommendations in solution/sources recommendation 706 and performs the next step.

VMAI 700 includes, among other things, application 701 (210, 312, 412), laboratories (Labs) and biometric monitoring devices 702 ($410_1$ to $410_n$), medical information database 703 (102), artificial intelligence (AI) 704 (103), medical library/findings/research results database 705 (102), and solution/sources recommendation 706.

In one embodiment of VMAI 700, artificial intelligence 704 performs the function of a trained medical doctor and surgeon.

In one embodiment of VMAI 700, artificial intelligence 704 is co-located with the application 701.

In one embodiment of VMAI 700, artificial intelligence 704 (103) resides on a remote server in a cloud.

In one embodiment of VMAI 700, medical information database 703 (102) is stored on a server in a cloud.

In one embodiment of VMAI 700, medical library/findings/research results database 705 (102) is stored on a server in a cloud.

In one embodiment of VMAI 700, Test LAB 702 is mobile and performs certain tests at a location specified by the patient.

In one embodiment of VMAI 700, Test LAB 702 is stationary and performs certain tests at a specific location.

In one embodiment of VMAI 700, a packet protocol is used for communication between different components of VMAI (application 701, Labs and biometric devices 702, medical information database 703, AI 704, Medical library 705, and recommendation and sources 706).

In one embodiment of VMAI 700, all the medical records and test results of the patient which are stored in medical information database 703 are used by artificial intelligence when activated by the patient through application 701 to provide a comprehensive recommendation.

In one embodiment of VMAI 700, all recorded and stored medical information, medical library, findings, experiences, medical research results, and the patient test results are used by artificial intelligence 704 when activated by a patient through application 701 to provide a recommendation.

In one embodiment of VMAI 700, artificial intelligence 704 uses all previous and recent test results, treatments, prescription and previous recommendations in its search for best and comprehensive new recommendations.

In one embodiment of VMAI 700, artificial intelligence 704 uses the inputs from the patient through application 701, and all previous and recent test results, treatments, prescription and recommendations in its search for best and comprehensive new recommendations.

In one embodiment of VMAI 700, the inputs from the patient through application 701 are real time biometric test results, and patient medical status and symptoms.

In another embodiment of VMAI 700, all medical status and symptoms that the patient provides to the artificial intelligence 704 through application 701 is in form of text, graph, recorded audio, image, recorded video, or other means.

In another embodiment of VMAI 700, the medical information data stored in medical information database 703 can be in form of text, graph, recorded audio, image, recorded video, and other means.

In one embodiment of VMAI 700, medical library/findings/research results database 705 can be in form of text, graph, recorded audio, image, recorded video, and other means.

In one embodiment of VMAI 700, application 701 can display various lab test results and biometric device results numerically and graphically on IoT (UE) 200 screen.

In one embodiment of VMAI 700, application 701 can display output of various biometric devices numerically and graphically in real time.

In one embodiment of VMAI 700, the recommendation provided by artificial intelligence 704 includes a number of options available to the patient.

In one embodiment of VMAI 700, application 701 and the local artificial intelligence (AI) operate on a smart phone, laptop, personal computer (PC), tablet, and any other wireless and wired communication device or equipment.

In another embodiment of VMAI 700, application 701 uses an IoT (UE) device and communicates with AI 103 (704) and database 102 (703, 705, and 706) using 4G, 5G, 6G or WiFi network.

In one embodiment of VMAI 700, all the wireless and wired communications between various components of VMAI 700 are encrypted, secured and protected.

In one embodiment of VMAI 700, a modeling language which is any artificial language to express information or knowledge or systems in a structure that is defined by a consistent set of rules is used.

In one embodiment of VMAI 700, various database languages are used for read, update and store data in a database.

In one embodiment of VMAI 700, all the wireless and wired communications between various components of VMAI 700 use an industry defined modeled language like YANG (yet another next generation) or other modeled languages sent over the NETCONF network configuration protocol.

In one embodiment of VMAI 700, application 701 uses wireless or wire to communicate with test labs and biometric devices 702, medical information database 703, artificial intelligence (AI) 704, medical library/findings/research results database 705, and solution/sources recommendation 706.

Figure 8:
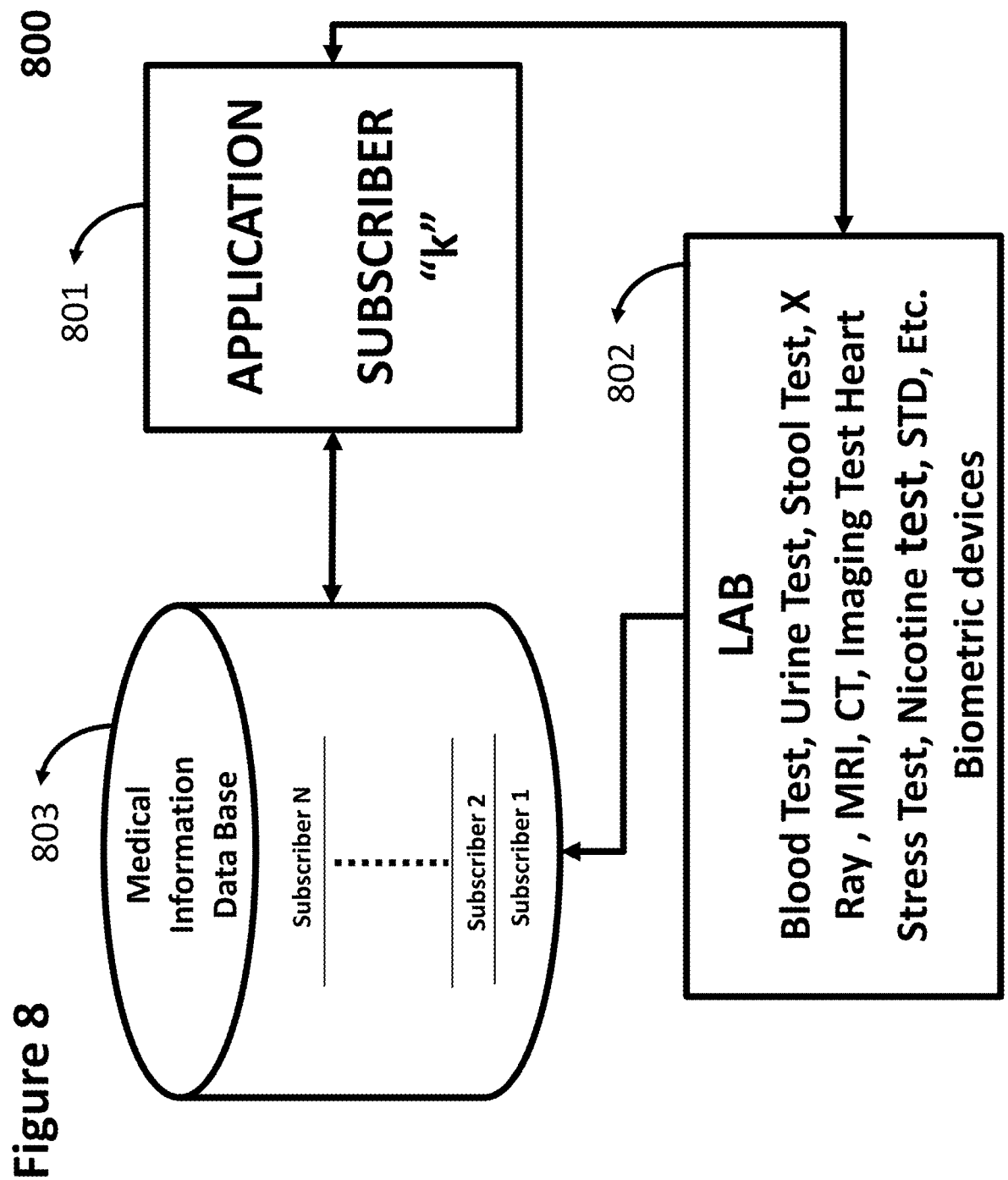
FIG. 8 depicts the mechanism medical data information is obtained and stored

FIG. 8 illustrates the mechanism medical information data is obtained and stored (MDS) 800. In general, MDS 800 provides a mechanism to obtain Laboratory (lab) test results, treatment results, biometric monitor device information data and patient's medical status and symptoms and store them in a central database. A patient through application 801 arranges for Lab tests from Laboratory 802, initializes, configures and controls biometric monitoring devices 802 attached to the patient's body, and inputs symptoms and treatment results data using at least one of a text, a graph, an image, a recorded audio, a recorded video and other means. AI Lab test results, biometric monitoring medical information data from 802, treatment results data and patient's medical status and symptoms are sent to medical information database 803 (102) for storage. The medical information database 803 (102) stores all the data with patient's name, date, time, and source of the data.

The MDS 800 includes among other things, application 801 (210, 312, 412), test Labs and biometric monitoring devices 802 ($410_1$ to $410_n$), and medical information database 803 (102).

In one embodiment of MDS 800, application 801 (210, 312,412) links a patient to biometric monitoring devices and various stationary and mobile test Labs 802 ($410_1$ to $410_n$).

In one embodiment of MDS 800, the patient through application 801 initializes and configures the parameters of the biometric monitoring devices 802 ($410_1$ to $410_n$) that are attached to the body of the patient and through wire or wireless communicate with the application 801 (210, 312, 412).

In one embodiment of MDS 800, the patient through application 801 (210, 312, 412) arranges an appointment with stationary test lab 802 ($410_1$ to $410_n$) to perform various tests.

In one embodiment of MDS 800, the patient through application 801 (210, 312, 412) arranges an appointment with mobile test lab 802 ($410_1$ to $410_n$) to perform various tests at a location specified by the patient.

In one embodiment of MDS 800, biometric monitoring devices 802 ($410_1$ to $410_n$) use wire or wireless communication to send the monitored results to medical information database 803 (102) for storage through application 801 (210, 312, 412).

In one embodiment of MDS 800, biometric monitoring device 802 ($410_1$ to $410_n$) acts as an Internet of Things (IoT) and use wire or wireless communication to send the monitored results to medical information database 803 (102) directly through IoT network (4G, 5G, WiFi).

In one embodiment of MDS 800, the data exchanged between biometric monitoring devices 802 and medical information database 803 uses an industry modeled language.

In one embodiment of MDS 800, mobile and stationary test labs 802 ($410_1$ to $410_n$) use wire or wireless communication to send the test results to medical information database 803 (102) for storage using IoT network (4G, 5G, WiFi).

In one embodiment of MDS 800, the data exchanged between mobile and stationary test labs 802 and medical information database 803 uses an industry modeled language.

In one embodiment of MDS 800, mobile and stationary test labs 802 ($410_1$ to $410_n$) use wire or wireless communication to send the test results to medical information database 803 (102) for storage through application 801 (210, 312, 412).

In one embodiment of MDS 800, application 801 (210, 312, 412) operates on an IoT (UE) device such as smart phone, laptop, PC, tablet, and any wireless or wired communication device or equipment.

In one embodiment of MDS 800, biometric monitoring devices 802 measure blood pressure, blood oxygen, body temperature, heart rate, blood sugar, electrocardiogram, sleep apnea measurements, various exercise parameters (such as calories used, and distance walked, ran, or biked) and other patient's internal and external body medical information data.

In one embodiment of MDS 800, the patient through application 801 arranges with various stationary and mobile Labs to perform various medical tests and send the test results to medical information database 803 directly or through application 801.

In one embodiment of MDS 800, application 801 (210, 312, 412) uses send box to send the patient's medical information using at least one of a text, a graph, an image, a recorded audio, a recorded video or other means.

In one embodiment of MDS 800, application 801 (210, 312, 412) uses an inbox to receive the patient's medical information data in form of at least one of a text, a graph, an image, a recorded audio, a recorded video, and other means.

In one embodiment of MDS 800, stationary and mobile labs 802 ($410_1$ to $410_n$) measure various blood tests, urine tests, Stool Tests, X Ray, MRI, CT scan, imaging tests, ultrasound tests, bone scan test, Heart Stress Test, heart related tests, Nicotine test, drug test, STD tests, physical tests and any other tests.

In one embodiment of MDS 800, medical information database 803 (102) receives the test information data from various biometric monitoring devices, mobile and stationary test labs and tag and store them base on name of the patient, day and time received, name and address of various labs, and name, identification or serial number of monitoring devices.

In one embodiment of MDS 800, medical information database 803 (102) informs the patient through application 801 (210, 312, 412) of any new test results received and provides access to them through application 801.

Figure 9:
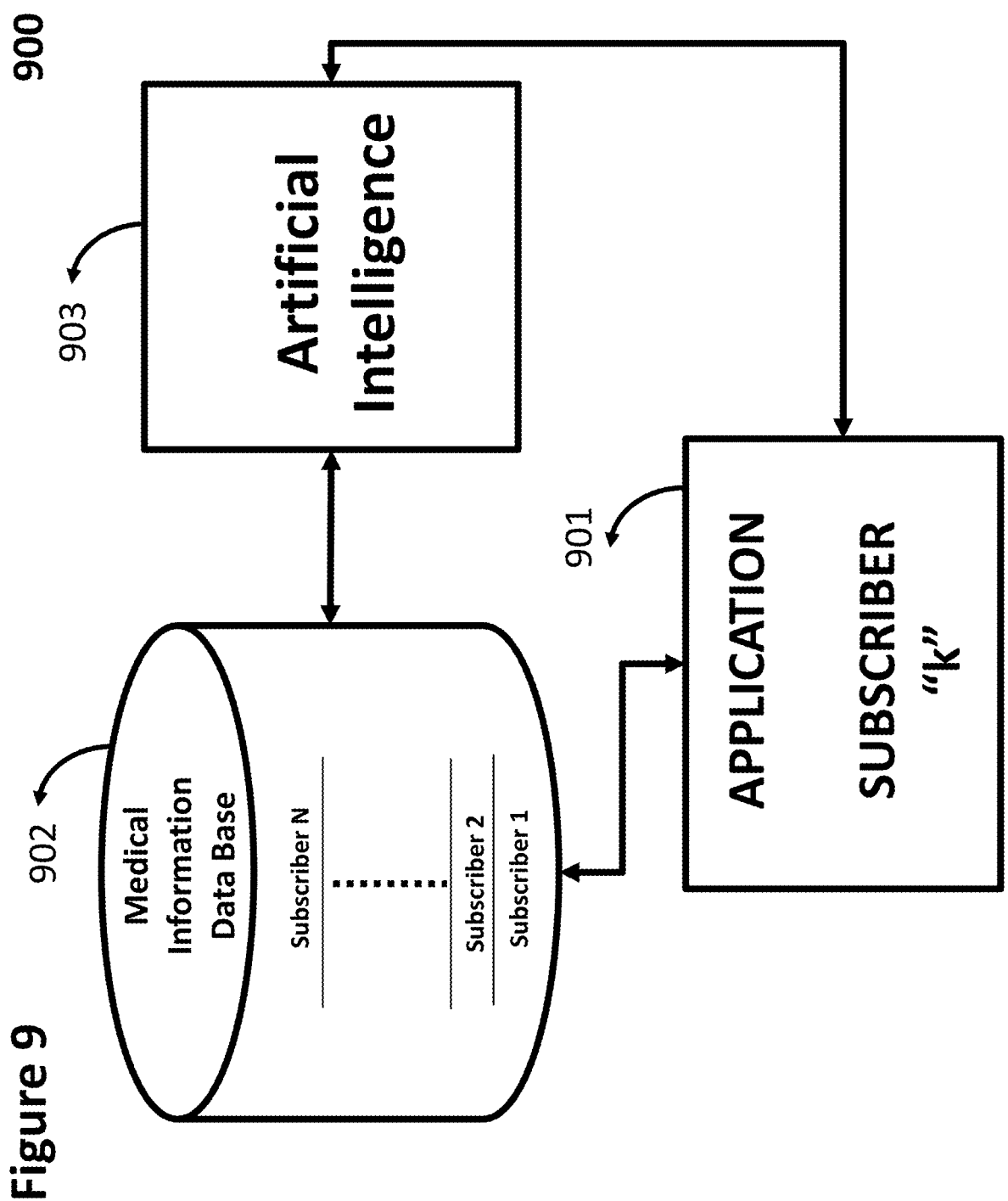
FIG. 9 shows the procedure the medical data information is obtained by artificial intelligence

FIG. 9 depicts the medical information data retrieval by artificial intelligence (DRA) 900. In general the DRA 900 is the procedure the medical information data is obtained by artificial intelligence.

The DRA 900 includes among other things application 901 (210, 312, 412), medical information database 902 (102), and artificial intelligence 903 (103).

In one embodiment of DRA 900, the patient through application 901 (210, 312, 412) sends medical status, symptoms and treatment results information data using at least one of a text, a graph, an image, a recorded audio a recorded video and other means to medical information database 902 (102) to be stored.

In one embodiment of DRA 900, the patient through application 901 (210, 312, 412) sends medical status, symptoms, and any real time biometric device medical information data to artificial intelligence 903 (102).

In one embodiment of DRA 900, the patient is informed of new test results to review through application 901 by medical information database 902.

In one embodiment of DRA 900, the patient through application 901 (210, 312, 412) accesses the new test results stored in medical information database 902 (102), study them, compare them with earlier results if any available.

If patient finds any test results that need attention then through application 901 (210, 312, 412) activates artificial intelligence 903 (103) for recommendation on solution and sources.

In one embodiment of DRA 900, when the patient through application 901 is informed of new test results then through application 901 activates artificial intelligence 903 for recommendation on solution and sources.

In one embodiment of DRA 900, when artificial intelligence 903 (103) is activated by the patient, then it will obtain all necessary patients' test results and any available medical status and symptom information that are stored in medical information database 902 (102) and uses them to come up with any recommendation on solutions and sources.

Figure 10:
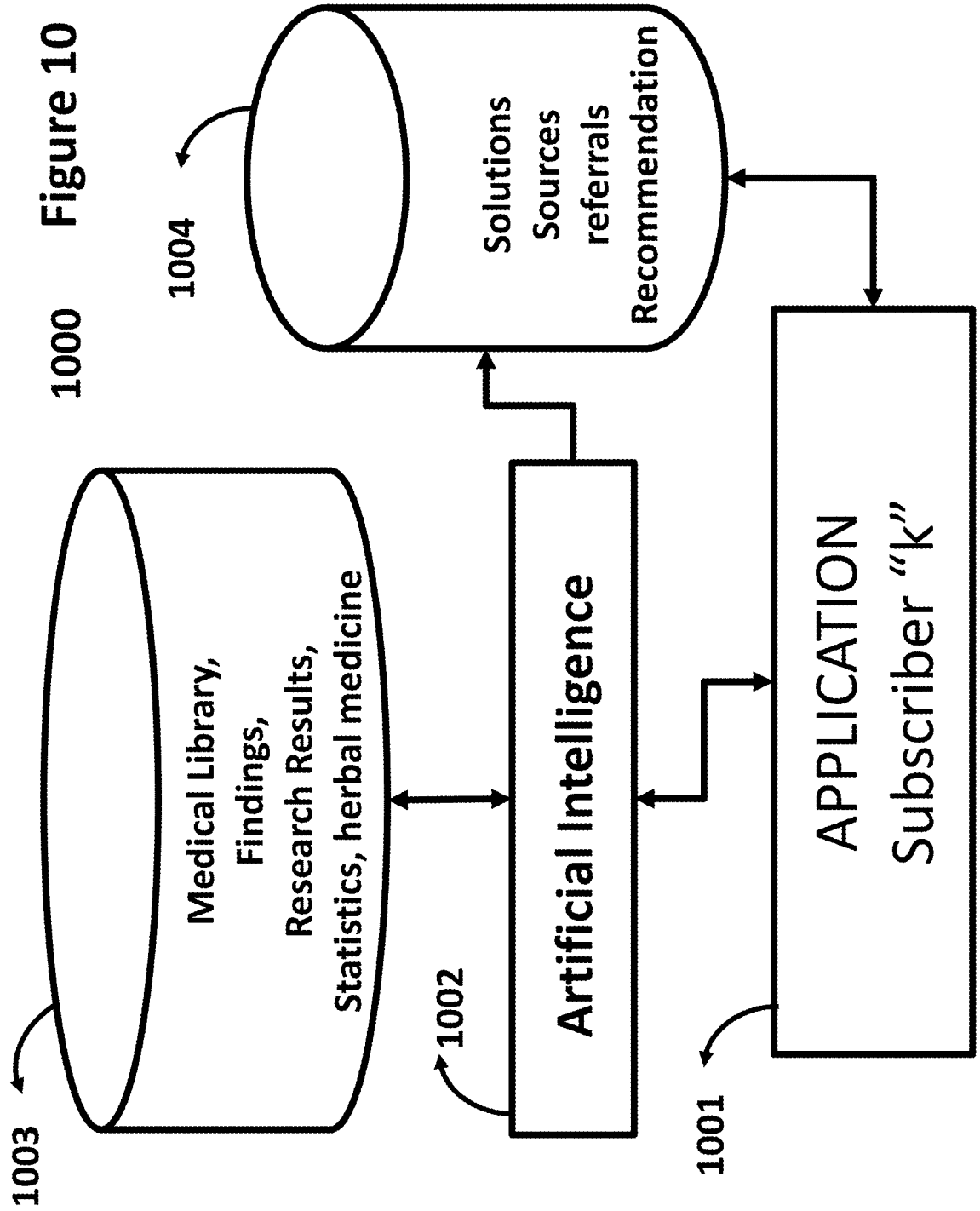
FIG. 10 shows the procedure used by artificial intelligence to provide recommendation to subscriber or patient

FIG. 10 depicts the procedure used by artificial intelligence to provide recommendation (PAR) 1000. In general the PAR 1000 by using a patient's test results and medical status information data provides recommendation for solutions and sources.

PAR 1000 includes, among other things, application 1001 (210, 312, 412), artificial intelligence 1002 (103), Medical Library, Findings, Research Results database 1003 (102), and solutions/sources recommendations 1004 (102).

In one embodiment of PAR 1000, the patient through application 1001 (210, 312, 412) requires first to register with virtual medical system 700 and creates an account with user identification (ID) and a password. In order to have access to database 1003 (102) and being able to activate AI 1002 (103) patient needs to sign in with user ID and password. This way both AI 1002 (103) and database 1003 (102) recognize the user of application 1001 (210, 312, 412). As part of registration patient provides name, address, phone number, email address, age, height, weight, social security number (if needed), medical insurance information, location coordinates, and any other information that is required.

In addition to patients, doctors, ERs (emergency rooms), EMS (emergency medical service), clinics, hospitals, laboratories and other entities that provide medical services also register with virtual medical system 700 with their detail information (name, address, phone number, website, type of service, license number, and any other detail information that requires for registration) similar to a patient and create an account with ID and password. The detail information of doctors and the other entities will be stored in database 102 (703, 705, and 706) to be used by patient, stationary and mobile labs as well as AI 103.

In one embodiment of PAR 1000, artificial intelligence 1002 (103) after being activated by the patient through application 1001 (210, 312, 412) retrieves the necessary patient's stored medical test results and symptoms information data, studies them and then uses the medical library/findings/research database 1003 (102) to come up with a solution recommendation or sources recommendation that can provide a comprehensive next step to the patient.

In one embodiment of PAR 1000, the patient uses application 1001 (210, 312, 412) to activate artificial intelligence 1002 (103) and to report patient's present medical problems and symptoms using text, graph, image, recorded audio and video or other means.

In one embodiment of PAR 1000, the communication between the patient through application 1001 (210, 312, 412) and artificial intelligence 1002 (103) is interactive and real-time.

In one embodiment of PAR 1000, artificial intelligence 1002 (103) while studying the patient's information data can ask the patient through application 1001 (210, 312, 412) for more information, medical history, or family medical history interactively and real-time.

In one embodiment of PAR 1000, artificial intelligence 1002 (103) after being activated by the patient through application 1001 (210, 312, 412) uses the patient's present medical problems and symptoms information data to retrieve necessary patient's stored test results and studies them and consult medical library database 705 (102) in order to provide a comprehensive next step recommendation to the patient through solutions/sources recommendations 1004.

In one embodiment of PAR 1000, artificial intelligence 1002 (103) sends the required lab tests and imaging tests also to appropriate test labs and imaging facilities ($410_1$ to $410_n$) directly or through application 1001 (210, 312, 412).

In one embodiment of PAR 1000, artificial intelligence 1002 (103) also uses Medical Library, Findings, Research Results database 1003 (102) to come up with recommendation.

In one embodiment of PAR 1000, artificial intelligence 1002 (103) asks the patient through application 1001 (210, 312, 412) for real time monitored medical information data from biometric devices connected to the patient body ($410_1$ to $410_n$).

In one embodiment of PAR 1000, artificial intelligence 1002 (103) asks the patient through application 1001 (210, 312, 412) for real time information data from monitoring biometric devices connected to body of the patient ($410_1$ to $410_n$) when patient performs certain physical functions.

In one embodiment of PAR 1000, the solution recommendation includes traditional herbal drugs, amount and duration of taking them.

In one embodiment of PAR 1000, the solution recommendation includes chemical drugs, amount and duration of taking them.

In one embodiment of PAR 1000, the solution recommendation includes the drug store information where to purchase and pick up the drugs.

In one embodiment of PAR 1000, the solution recommendation includes performing various lab tests, imaging tests and the detail medical information data required from the tests.

In one embodiment of PAR 1000, the solution recommendation includes performing certain physical exercise.

In one embodiment of PAR 1000, the solution recommendation includes having specific diet.

In one embodiment of PAR 1000, the solution recommendation includes performing certain treatments using certain drugs, physical and mental activities or other means of treatment.

In one embodiment of PAR 1000, the solution recommendation includes use of various biometric monitoring devices by the patient.

In one embodiment of PAR 1000, the solution recommendation includes type of doctor, surgeon, clinic, and hospital the patient needs to visit and present the artificial intelligence recommendation.

In one embodiment of PAR 1000, the source recommendation includes name and address of the test labs that patient needs to visit to perform certain tests.

In one embodiment of PAR 1000, the recommendation includes the configuration and test parameters of the biometric monitoring devices.

In one embodiment of PAR 1000, the source recommendation includes name and address of the doctors, surgeons, clinics, hospitals and other entities that provide medical services the patient needs to visit.

In one embodiment of PAR 1000, the patient through application 1001 (210, 312, 412) is informed of presence of recommendation.

In one embodiment of PAR 1000, the patient uses the recommendations for the next step in the treatment.

In one embodiment of PAR 1000, the patient uses the recommendation from solutions/sources recommendations 1004, to perform the next steps that include performing lab test, imaging test, taking herbal or chemical drugs, collecting biometric medical information data, seeing a recommended doctor (clinic, hospital or other entities that provide medical services) and storing the results information data in the medical information database (102).

In one embodiment of PAR 1000, after the patient performed the next step recommendations and stored the results, then if needed activates the artificial intelligence 1002 (103) again for comprehensive next step recommendation and sources.

FIGS. 11A through 11K shows the artificial intelligence (AI) algorithm 2000. AI algorithm 2000 has access to database 102 in the cloud 101, application 210 (312, and 412) in IoT (UE) device 200 (300, and 400), and external device 310 (410$_1$ to 410$_n$) directly or through application 210 (312, and 412). AI algorithm 2000 accesses the external device 310 (410$_1$ to 410$_n$) in real-time or at specific times. External device 310 (410$_1$ to 410$_n$) can communicate with AI algorithm 2000 through 4G, 5G, or WiFi network or through application 210 (312 and 412).

AI algorithm 2000 sends and receives information data to and from application 210 (312 and 412). AI algorithm 2000 receives information data from external device 310 (410$_1$ to 410$_n$) and in special case demands certain information data from external device 310 (410$_1$ to 410$_n$).

AI 103 is a pool of AI algorithms. AI 2000 is a main algorithm that is related to general medical conditions which identifies the nature of medical problem and provides recommendation, treatment, solution, prescription, sources and referral to other entities or AI algorithms within AI 103 pool that specialized in details of a medical condition as well as entities that perform surgeries. Other artificial intelligence algorithms in AI 103 pool relate to special medical conditions and are not included in AI 2000.

Patient signs in to application 210 (312, and 412) which is on his/her cell phone or any other device and check the application inbox for any information data as well as activates its connection to AI 103 and start communication and transmitting information data at 2001. At 2002 patient sends his/her medical status and symptoms and performs real-time communication with AI 103 and answers potential questions from AI 103. At 2003 AI 103 studies the medical status and symptoms of patient and analyses them using medical library and patient's medical information data in information database 102. At 2004 if more information from patient is required AI 103 ask the patient at 2002 until no more information from patient is required at stage 2004. At stage 2005 AI 103 decides if this is a life threatening case. If the answer is yes at 2006 AI 103 calls 911 and provides detail patient information to 911 operators. Patient information includes patient name, address (location), medical status, phone number, gender, age and information about patient surrounding and circumstances.

On page 11B at 2007 AI 103 checks if this case requires EMS (emergency medical services). If yes at 2008 AI 103 by using medical library in information database 102 establishes type of out-of-hospital treatment required and is available. Then at 2009 AI 103 contacts a local control facility with detail patient information and asks to dispatch a suitable resource to deal with patient situation.

If this is not an EMS situation at 2010 AI 103 checks to see if medical status of the patient requires a visit to ER (emergency room). If it does at 2011 AI 103 provides detail information for suitable local ER for the patient to visit. If it is not an ER case then it is an outpatient case and will be treated based on procedures shown in FIG. 11C to 11K.

Figure 11A:
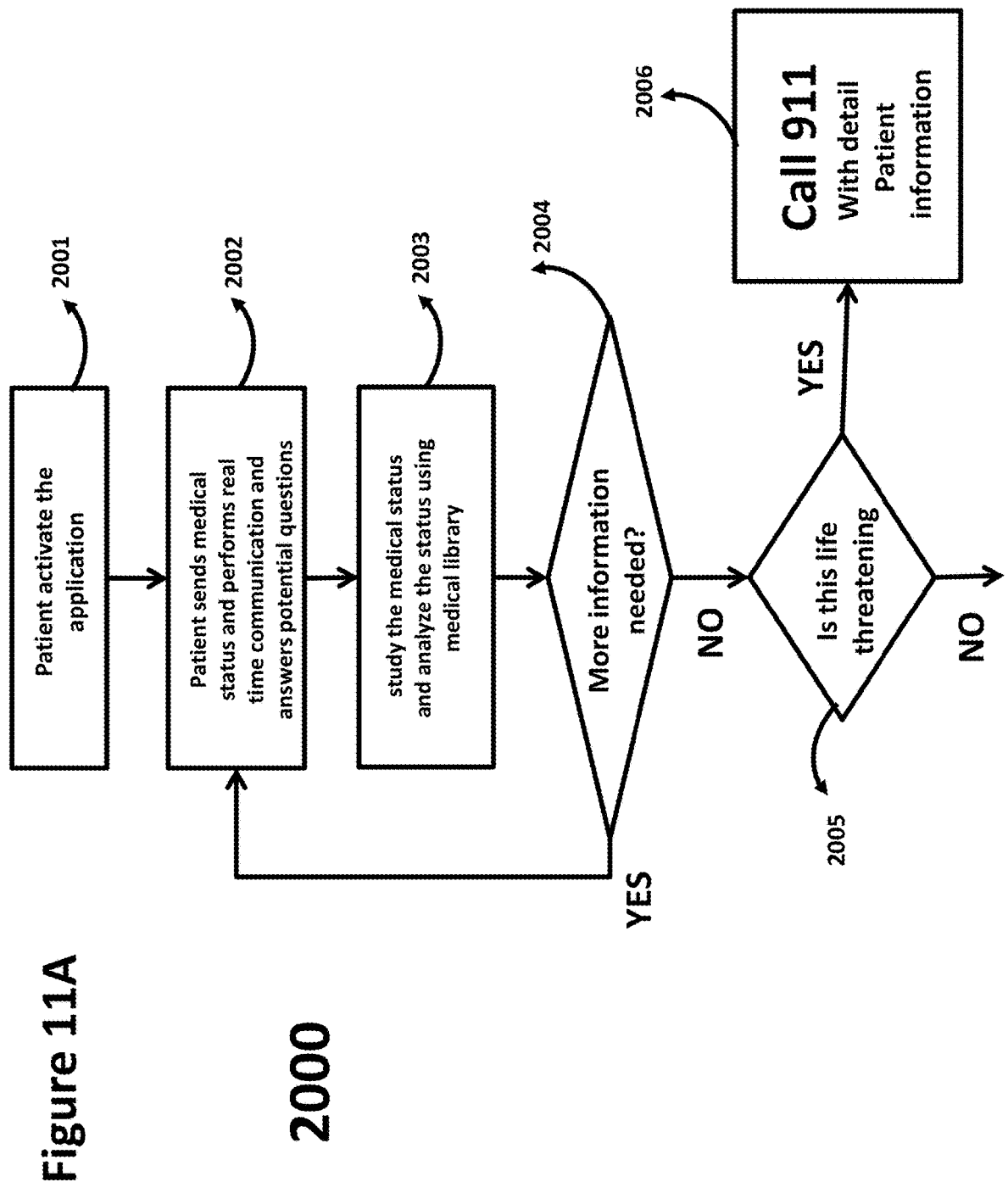
Figure 11B:
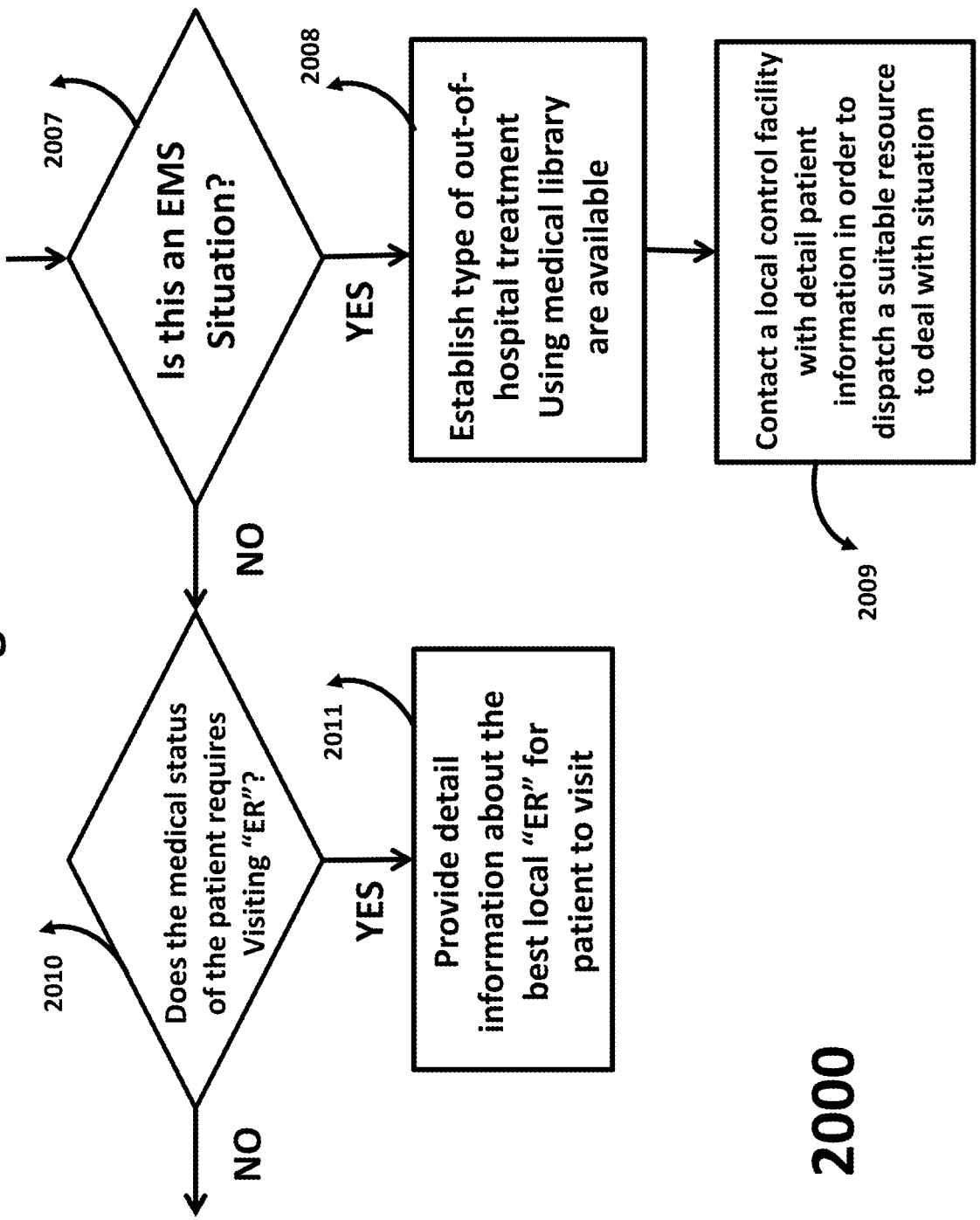
Figure 11C:
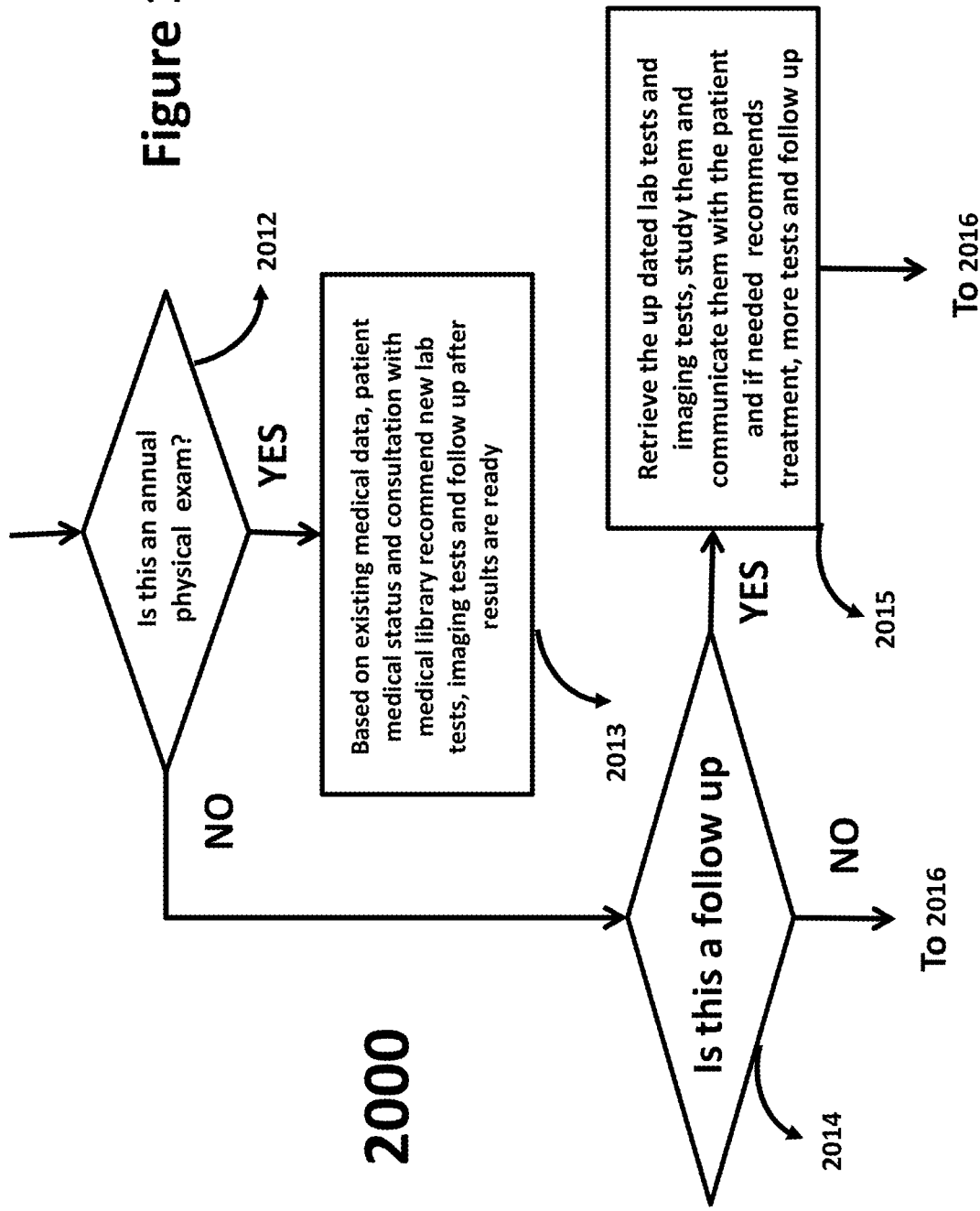

FIG. 11C and following figures show the outpatient treatment. At 2012 AI 103 decides it patient needs annual checkup. If the answer is positive then based on existing patient's medical information data in database 102 and present medical status provided by patient then at 2013 AI 103 consults with medical library in database 102 and recommends new lab tests and imaging test and follow up after the results are ready. If this is not an annual examination at 2014 AI 103 checks If this is follow up and then AI 103 retrieves the up dated lab tests and imaging tests, study them and communicate them with the patient. Then AI 103 either recommends treatment with prescription drug or proceeds to 2016. If it is not a follow up AI 103 proceeds to 2016.

At 2016 AI 103 retrieves patient's old and new medical data from database 102. AT 2017 AI 103 studies patient's medical information data from database 102 and present medical status and symptoms. At 2018 AI 103 consults medical library in database 102 and at 2019 decides if more information is needed. If the answer is positive at 2020 AI 103 communicates with patient and gets more information and goes to step 2018 to consult the medical library in database 102 and continues to step 2019 and repeats this loop until there is no need for more information. When AI 103 has all the information needed then at 2021 studies all medical information and proceeds to 2022.

Figure 11E:
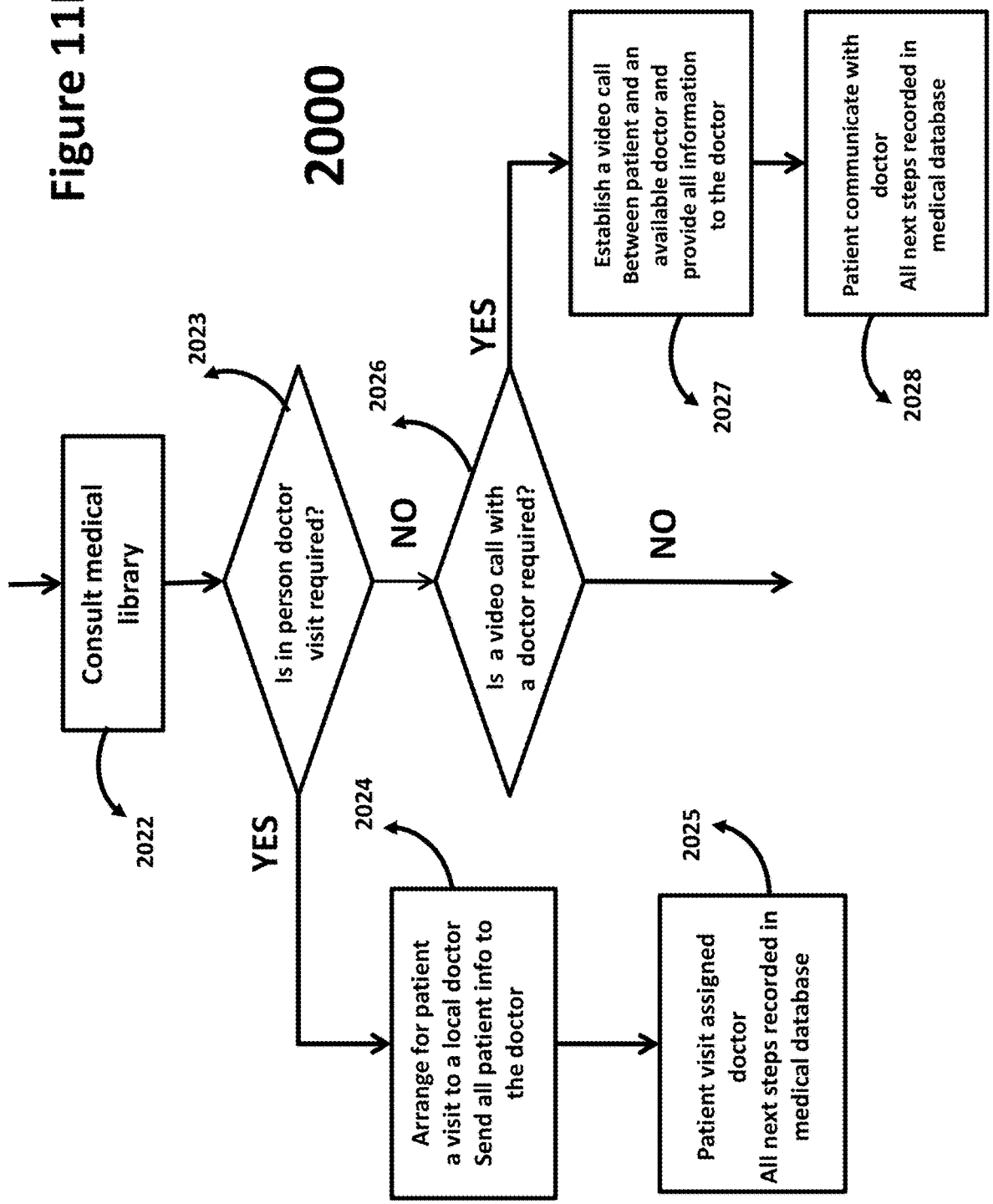

FIG. 11E shows the procedure of deciding if an in person doctor visit or a video call with a doctor needed. At 2022 AI 103 consults medical library in database 102. Based on consultation with medical library at 2023 AI 103 decides if an in person visits to a doctor due to need for physical examination is required. If the answer is positive then at 2024 AI 103 arranges for patient a visit to a local doctor and sends patient's medical information data to the doctor. The doctor performs outpatient surgery, refers the patient to a psychologist, a neurologist or any other doctor as appropriate. At 2025 patient visits assigned doctor and all next steps will be recorded in database 102 for possible follow up if needed.

In case there is no need for in person visit to a doctor then AI 103 at 2026 decides if a video call with a doctor is required. If the answer is positive then at 2027 AI 103 establishes a video call between patient and an available doctor and provides patient's medical information data to the doctor. At 2028 patient communicates with doctor. The doctor based on video inspection of the patient advises the patient what steps patient needs to take and all next steps will be recorded in medical database 102 for possible follow up. If there is no need for a video call with a doctor then AI 103 proceeds to step 2029.

In next step AI 103 identifies if the patient needs to visit a certain specialist based on patient's medical status, symptoms, medical information data and result of consultation with medical library. The specialist is at least one of a doctor, an artificial intelligence (AI) algorithm specific to that field of medical condition, and a robot trained as a doctor. The AI specialist is an algorithm for a specific medical condition. AI 2000 acts as a general practitioner.

Figure 11F:
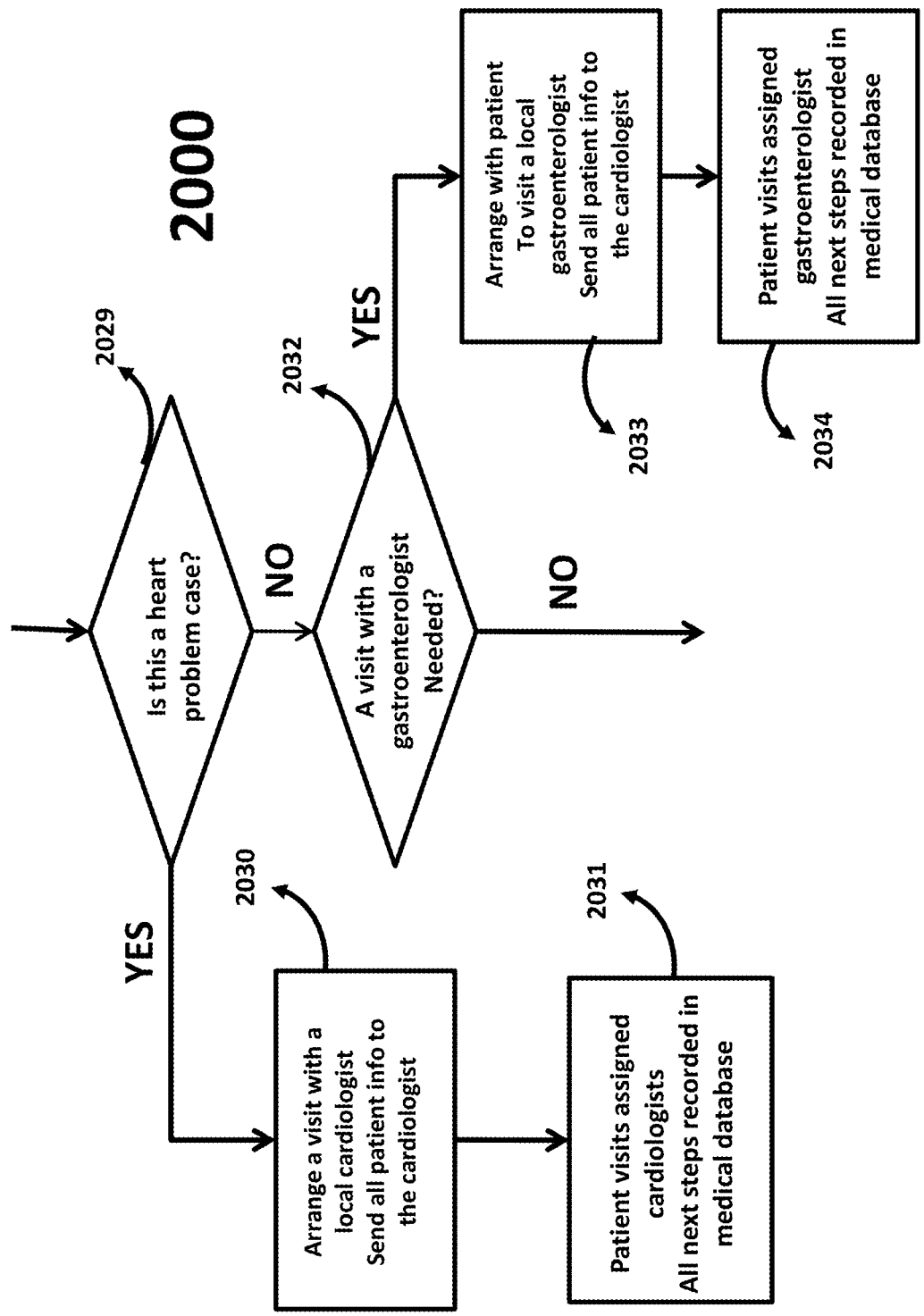

As shown in FIG. 11F at 2029 AI 103 determines if the patient's medical information data and result of medical library consultation points to heart problem. If the answer is positive then at 2030 AI 103 arranges for patient a visit with a local cardiologist and sends patient's medical records to the cardiologist. At 2031 patient visits assigned cardiologists and all next steps will be recorded in medical database 102.

At 2032 AI 103 determines if the patient's medical information data and result of medical library consultation points to digestive system problem. If the answer is positive then at 2033 AI 103 arranges for patient a visit with a local gastroenterologist and sends patient's medical records to the gastroenterologist. At 2034 patient visits assigned gastroenterologist and all next steps will be recorded in medical database 102.

If AI 103 identifies that patient's medical problem is not related to heart and digestive system then it goes to step 2035.

Figure 11G:
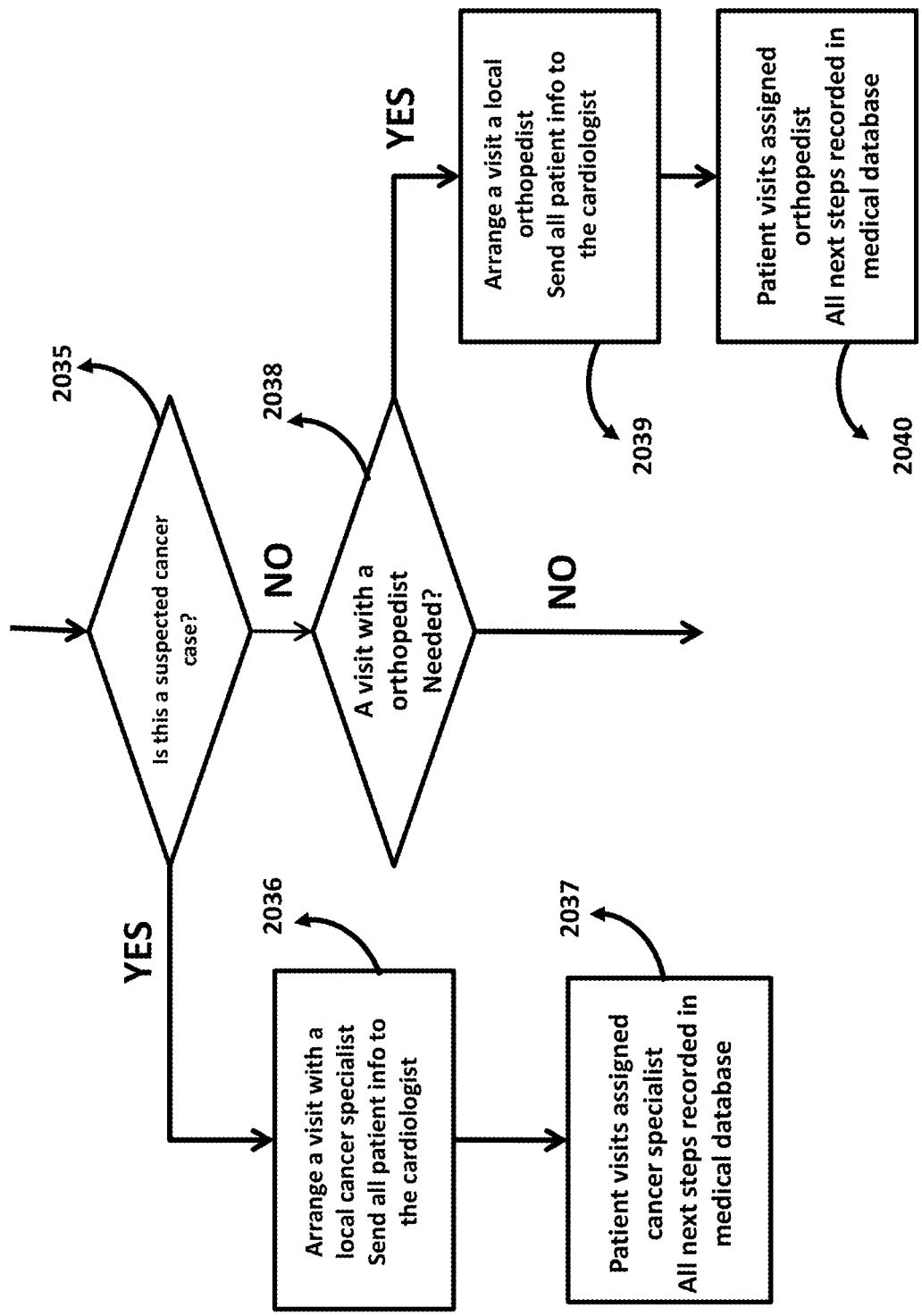

FIG. 11G shows that at 2035 AI 103 determines if the patient's medical information data and result of medical library consultation points to potential cancer. If the answer is positive then at 2036 AI 103 arranges for patient a visit with a local cancer specialist and sends patient's medical records to the local cancer specialist. At 2037 patient visits assigned local cancer specialist and all next steps will be recorded in medical database 102.

At 2038 AI 103 determines if the patient's medical information data and result of medical library consultation points to bone related problem. If the answer is positive then at 2039 AI 103 arranges for patient a visit with a local orthopedist and sends patient's medical records to the orthopedist. At 2040 patient visits assigned orthopedist and all next steps will be recorded in medical database 102.

If AI 103 identifies that patient's medical problem is not related to cancer and bone then it goes to step 2041.

Figure 11H:
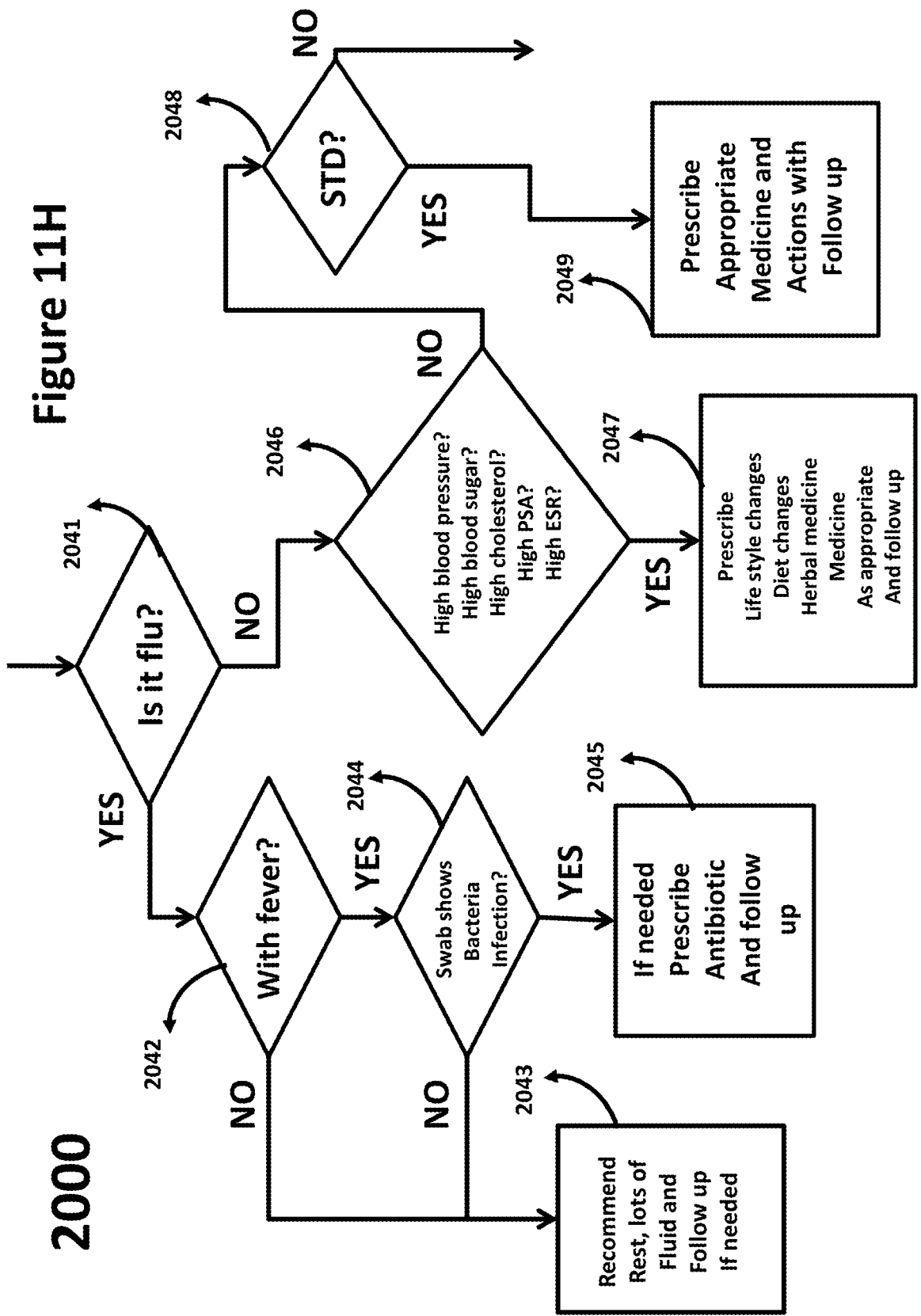

FIG. 11H shows that at 2041 AI 103 determines if patient's medical condition is flu. If the answer is positive then at 2042 for flu with no fever AI 103 at 2043 recommends rest, lots of fluid and a follow up if needed. If flu is with fever at 2044 from swab test result determines if it is bacterial infection or viral infection. If the answer is negative recommends step 2043, and for positive answer at 2045 AI 103 if needed prescribes antibiotic, medicine, rest and follow up.

If the medical symptoms of patient are not flu then at 2046 AI 103 looks for high blood pressure, high blood sugar, cholesterol, high PSA, high ESR and other reasons from tests results and present symptoms. Then if the answer is positive at 2047 prescribes life style changes, diet changes, herbal medicine, and medicine as appropriate with follow up. If the answer at 2046 is negative then goes to step 2048.

At 2048 AI 103 determines if the patient's medical condition is due to STD (sexual transmitted diseases). If the answer is positive at 2049 prescribes appropriate medicine and action with follow up. If the condition is not due to STD then AI 103 goes to step 2050.

Figure 11I:
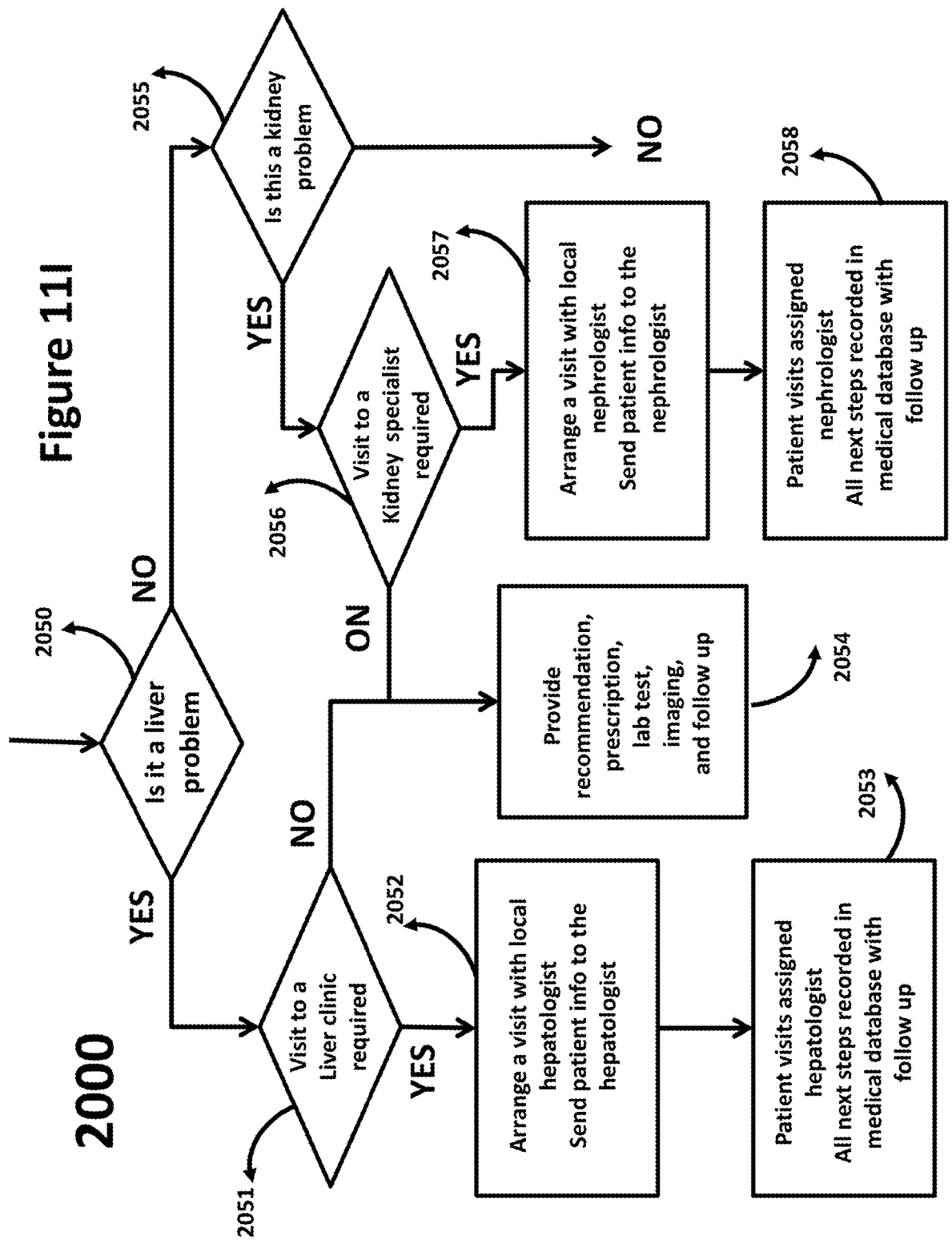

FIG. 11I depicts steps to take for liver and kidney problem. At 2050 AI 103 determines if patient has liver problem. If the answer is yes then at 2051 AI 103 identifies if a visit to a liver clinic is required. If the answer is positive then at 2052 AI 103 arranges a visit with local hepatologist and sends patient medical information data to the hepatologist. At 2053 Patient visits assigned hepatologist and all next steps recorded in medical database 102 with follow up. If there is no need to visit a liver clinic then at 2054 AI 103 provides recommendation, prescription, lab test, imaging test, and follow up. At 2050 if the answer is no then at 2055 AI 103 determines if patient has kidney problem. If the answer is yes then at 2056 AI 103 identifies if a visit to a kidney specialist is requires. If the answer is positive then at 2057 AI 103 arranges a visit with local nephrologist and sends patient medical information data to the nephrologist. At 2058 Patient visits assigned nephrologist and all next steps recorded in medical database 102 with follow up. If there is no need to visit a kidney specialist then at 2054 AI 103 provides recommendation, prescription, lab test, imaging test, and follow up.

At 2055 if the answer is no then AI 103 goes to step 2059.

Figure 11J:
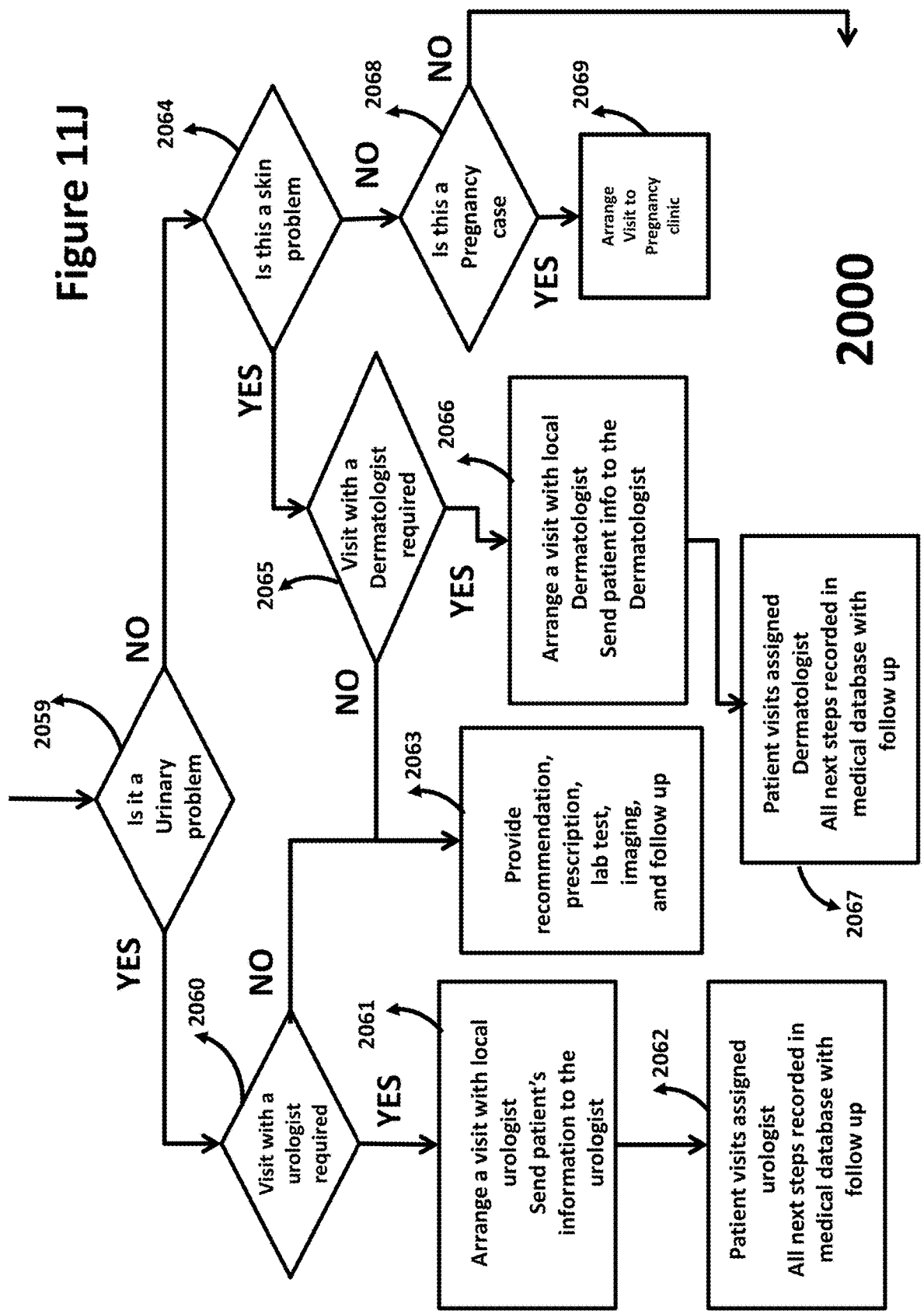
Figure 11K:
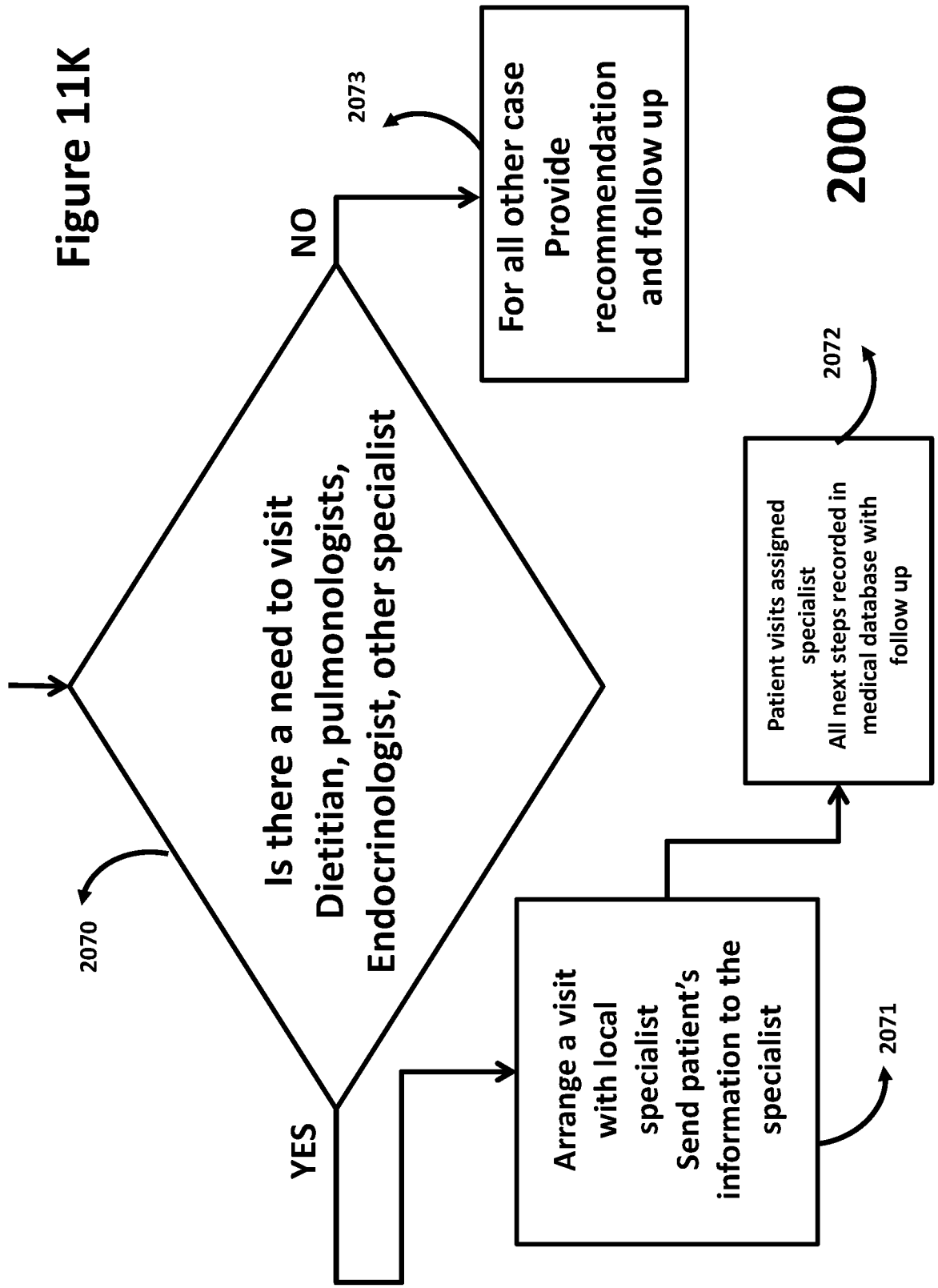

FIG. 11J illustrates steps to take for urinary and skin problem. At 2059 AI 103 determines if patient has urinary problem. If the answer is yes then at 2060 AI 103 identifies if a visit to a urologist is required. If the answer is positive then at 2061 AI 103 arranges a visit with local urologist and sends patient medical information data to the urologist. At 2062 Patient visits assigned urologist and all next steps recorded in medical database 102 with follow up. If there is no need to visit an urologist then at 2063 AI 103 provides recommendation, prescription, lab test, imaging test, and follow up. At 2059 if the answer is no then at 2064 AI 103 determines if patient has skin problem. If the answer is yes then at 2065 AI 103 identifies if a visit to a Dermatologist is requires. If the answer is positive then at 2066 AI 103 arranges a visit with local Dermatologist and sends patient medical information data to the Dermatologist. At 2067 Patient visits assigned Dermatologist and all next steps recorded in medical database 102 with follow up. If there is no need to visit a Dermatologist then at 2063 AI 103 provides recommendation, prescription, lab test, imaging test, and follow up.

At 2064 if the answer is no then AI 103 at 2068 determines if the patient case is pregnancy. If the answer is positive then at 2069 AI 103 arranges a visit to pregnancy clinic. If the answer is negative AI 103 goes to step 2070 in FIG. 11K.

At 2070 AI 103 determines if the patient case requires a visit to a dietitian, a pulmonologists, an endocrinologist, or another specialist. If the answer is positive then at 2071 AI 103 arranges a visit with a local specialist and sends patient's medical information data to the specialist. At 2072 patient visits assigned specialist and all next steps recorded in medical database 102 with follow up.

If the answer is negative at 2073 AI 103 for all other cases provides recommendation, prescription, lab tests, imaging tests, and a follow up.

The specialist's treatment can include a surgery that is performed by a surgeon, a team of surgeons, a remote surgeon using a robot, a team of surgeons using a robot, or a robot.

FIG. 12 shows an embodiment of a method 3000 for a virtual medical treatment. In various embodiments, method 3000 is carried out by an application, test Labs, biometric monitoring devices, medical information database, artificial intelligence, medical library, solutions and sources under the control of processes or executable instructions. The readable and executable instructions reside, for example, in a data storage medium such as processor usable volatile and non-volatile memory. However, the readable and executable instructions may reside in any type of processor readable storage medium. In some embodiments, method 3000 is performed at least by one of the steps described herein.

At 3001 of method 3000, a patient or subscriber signs in an application and through the application requests from test LABs for appointment to perform necessary tests and activates biometric monitoring devices for information data.

At 3002 of method 3000, test LAB performs the required tests, biometric monitoring devices provide the required information data and send the results to a medical information database for storage and subscriber or patient is informed of the results.

At 3003 of method 3000, the medical information database stores the subscriber or patient's information data in the subscriber or patient's memory location.

At 3004 of method 3000, the patient or subscriber accesses the test results, studies them and asks Artificial Intelligence to study the stored latest test results and subscriber or patient's direct medical inputs to recommend solution and sources.

At 3005 of method 3000, Artificial Intelligence studies all the stored test results and information data supplied by the patient or subscriber and uses the medical library, medical findings and research database and provides the patient or subscriber with recommendations.

At 3006 of method 3000, the patient or subscriber studies the artificial intelligence's recommendations and takes the next step.

Various embodiments are thus described. While particular embodiments have been described, it should be appreciated that the embodiments should not be construed as limited by such description, but rather construed according to the following claims.

The invention claimed is:

1. A virtual medical system comprising:
    an Internet of Thing (IoT) device that communicates with an IoT network that is at least one of a fifth generation wireless (5G) network, a sixth generation wireless (6G) network, and a wireless fidelity (WiFi) network to exchange an information data;
    said IoT network support a cloud that houses a database, and an algorithm that is executed by a sever;
    said IoT device also communicates and exchange said information data with at least one of a wearable IoT device, a stationary IoT laboratory (LAB), and a mobile IoT laboratory using a wired or a wireless link;
    said information data from said IoT network includes at least a time of day (TOD) that includes a date, and an absolute time specified by said algorithm;
    said absolute time is said TOD that includes at least one of said date, an hour, a minute, a second, a millisecond, and a microsecond;
    said TOD is obtained by said IoT device from said IoT network using a downlink unused sub-carrier of a primary synchronization sequence (PSS) or a secondary synchronization sequence (SSS);
    said TOD is used to keep said IoT devices, said IoT network and said cloud time synchronous;
    an application that resides in said IoT device and is used or activated by at least one of a patient, an individual, and a robot to:
    exchange said absolute time, and said TOD with said wearable IoT devices and program them to obtain a medical information data by performing a data collecting task;
    use the TOD and arrange with said stationary IoT LAB or said mobile IoT LAB to have a laboratory test and receive a LAB test information data;
    communicate real time with the cloud through said IoT network to exchange said medical information data and said LAB test information data in form of at least one of a text, an image, a graph, a recorded audio and a recorded video clip with said database and said algorithm; and
    receive a medical recommendation data from said algorithm in said cloud for a next step; or
    connect to a medical entity by said algorithm through said IoT network.

2. The virtual medical system of claim 1, wherein said database stores the patient's said medical information data and said LAB test information data received from at least one of said application, said mobile IoT LAB, said stationary IoT LAB, and said algorithm.

3. The virtual medical system of claim 1, wherein said algorithm and said database reside on said server and are virtualized in the cloud.

4. The virtual medical system of claim 1, further said algorithm and said application are co-located in said IoT device.

5. The virtual medical system of claim 1, wherein said database stores a medical resource that includes information about at least one of a physician, a clinic, a hospital, a drug, a drugstore, and a medical library.

6. The virtual medical system of claim 1, wherein said medical entity is at least one of a 911 operator, an EMS (emergency medical services), an ER (emergency room), a virtual physician, and a physician clinic.

7. The virtual medical system of claim 6, further said entity has access to the medical information data and the LAB test information data through said IoT network and said cloud.

8. The virtual medical system of claim 1, wherein said TOD is obtained by a GPS (global positioning system) receiver.

9. The virtual medical system of claim 1, wherein said TOD is obtained from said another IoT device using an Institute of Electrical and Electronic Engineering IEEE1588 protocol.

10. The virtual medical system of claim 1, further said absolute time contains at least one of a first microsecond in a millisecond, a Kth microsecond in a millisecond and a Nth microsecond in a millisecond of said TOD.

11. A method to provide a virtual medical service, said method comprising:
    virtualization of a database, and an algorithm on a server in a cloud used by an Internet of Things (IoT) network;
    using an IoT device to communicate with said IoT network to obtain a time of day (TOD) from said IoT network and an absolute time from said algorithm;
    installing a wearable IoT device on a body of a patient;
    installing an application in said IoT device to be used by said patient to:
    communicate with said wearable IoT devices, a mobile IoT laboratory (LAB), a stationary IoT LAB, said database and said algorithm;
    use said TOD to time synchronize said IoT devices with said IoT network, said algorithm, and said database;
    use said TOD and said absolute time to program said wearable IoT devices to collect a medical information data;
    use said TOD to arrange with said mobile IoT LAB and said stationary IoT LAB to perform LAB test and provide a LAB test information data; send said medical information data and said LAB test information data and a medical status of said patient to the cloud to be stored in the database and analyzed by said algorithm; and
    receive a recommendation data for a next step; or
    connect to a medical entity by said algorithm through said IoT network.

12. The method of claim 11, wherein said medical information data and said LAB test information data are in form of at least one of a text, an image, a graph, a recorded audio, and a recorded video.

13. The method of claim 12, wherein said algorithm retrieves needed information from said medical information data and the LAB test information data then analyze and make said recommendation for said next step.

14. The method of claim 13, further said next step is a prescription or referral to a virtual physician or a physician clinic.

15. The method of claim 13, wherein the LAB information data includes at least one of a blood test, an urine test, a Stool Test, a X Ray, a MRI, a CT, an imaging test, an ultrasound test, a bone scan test, a Heart Stress Test, a heart related test, a Nicotine test, a drug test, a STD test, a physical test, and any other test.

16. The method of claim 13, further said medical information data includes at least one of a medical status of said patient, a blood pressure, a body temperature, a heart rate, a blood sugar, an electrocardiogram, a sleep apnea, an exercise parameter (such as distance to walk, run, or bike) or other said patient's internal and external body medical data.

\* \* \* \* \*